United States Patent
Hamamatsu et al.

(10) Patent No.: US 7,315,366 B2
(45) Date of Patent: Jan. 1, 2008

(54) APPARATUS AND METHOD FOR INSPECTING DEFECTS

(75) Inventors: Akira Hamamatsu, Yokohama (JP); Minori Noguchi, Mitsukaido (JP); Yoshimasa Ooshima, Yokohama (JP); Hidetoshi Nishiyama, Fujisawa (JP); Tetsuya Watanabe, Honjyou (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 11/714,196

(22) Filed: Mar. 6, 2007

(65) Prior Publication Data

US 2007/0153264 A1 Jul. 5, 2007

Related U.S. Application Data

(63) Continuation of application No. 10/050,776, filed on Jan. 18, 2002, now Pat. No. 7,187,438.

(30) Foreign Application Priority Data

Mar. 1, 2001 (JP) ............................ 2001-056547

(51) Int. Cl.
*G01N 21/00* (2006.01)
(52) U.S. Cl. ................ 356/237.2; 356/237.4; 356/237.5
(58) Field of Classification Search ............... None
See application file for complete search history.

(56) References Cited

U.S. PATENT DOCUMENTS

| 5,903,342 | A | 5/1999 | Yatsugake et al. |
|---|---|---|---|
| 6,104,481 | A | 8/2000 | Sekine et al. |
| 6,657,736 | B1 | 12/2003 | Finarov et al. |
| 6,734,967 | B1 * | 5/2004 | Piwonka-Corle et al. ... 356/369 |
| 6,798,504 | B2 | 9/2004 | Sato et al. |
| 7,242,016 | B2 * | 7/2007 | Ishimaru et al. ....... 250/559.46 |
| 2001/0030296 | A1 | 10/2001 | Ishimaru et al. |
| 2002/0186367 | A1 | 12/2002 | Eytan et al. |

FOREIGN PATENT DOCUMENTS

| JP | 03-102248 | 4/1991 |
|---|---|---|
| JP | 03-102249 | 4/1991 |
| JP | 4-152545 | 5/1992 |
| JP | 06-222013 | 8/1994 |
| JP | 06-249791 | 9/1994 |
| JP | 09-304289 | 11/1997 |
| JP | 11-142127 | 5/1999 |
| JP | 11-160245 | 6/1999 |
| JP | 2000-105203 | 4/2000 |

* cited by examiner

*Primary Examiner*—Michael P. Stafira
(74) *Attorney, Agent, or Firm*—Antonelli, Terry, Stout & Kraus, LLP.

(57) ABSTRACT

A defect-inspecting apparatus including an arrangement to convert detected light into a first signal corresponding to light illuminated by a high-angle illumination optical system and/or a second signal corresponding to light illuminated by a low-angle illumination optical system; and a classification unit which utilizes the first and second signal and classifies defects on the object to be inspected, wherein a defect size is estimated by changing a correction coefficient of the defect size on a basis of a concave-convex level (b/a), where the concavo-convex level (b/a) of a defect is indicated by a ratio of a size b of a first direction of the defect to a size a of a second direction of the defect, where the second direction is lateral to the first direction.

5 Claims, 15 Drawing Sheets

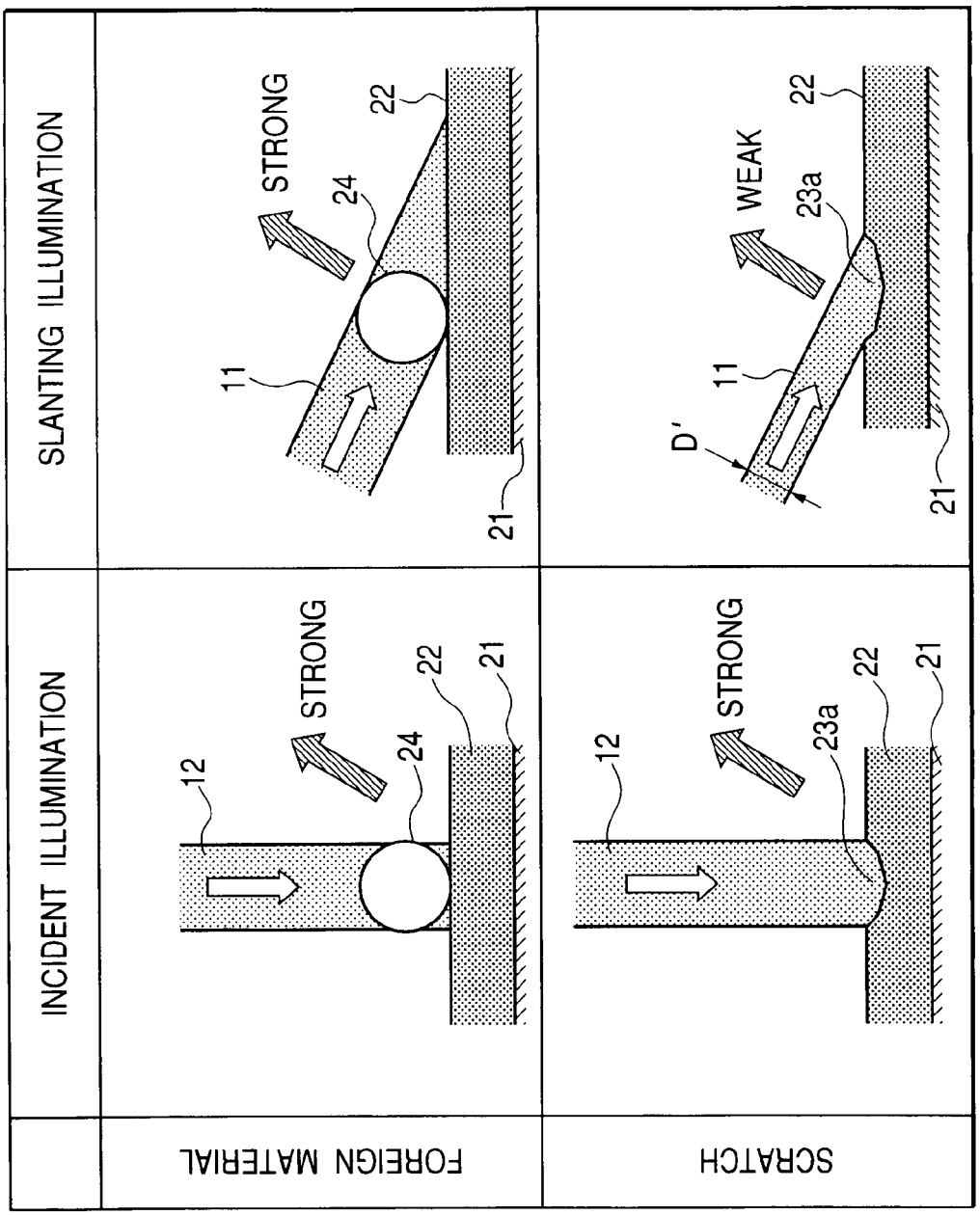

FRONT-END PROCESS WAFER

BACK-END PROCESS WAFER

| SIZE | SMALL | | LARGE |
|---|---|---|---|
| FOREIGN MATERIAL/ SCRATCH | FOREIGN MATERIAL | SCRATCH | — |
| ON PATTERN | CATEGORY 1 | CATEGORY 3 | CATEGORY 5 |
| OUTSIDE PATTERN | CATEGORY 2 | CATEGORY 4 | |

APPARATUS AND METHOD FOR INSPECTING DEFECTS

CROSS REFERENCE TO RELATED APPLICATION

This is a continuation of U.S. application Ser. No. 10/050,776, filed Jan. 18, 2002 now U.S. Pat. No. 7,187,438. This application relates to and claims priority from Japanese Patent Application No. 2001-056547, filed on Mar. 1, 2001. The entirely of the contents and subject matter of all of the above is incorporated herein by reference.

BACKGROUND OF THE INVENTION

The present invention relates to a defect-inspecting apparatus and a defect-inspecting method, which are used for inspecting defects such as a scratch or a particulate foreign material by discrimination; the defects occur in a planarization fabrication process based on polishing or grinding fabrication technique, which is used in semiconductor production and in magnetic head production.

As a prior art that inspects a foreign material, which adheres to a semiconductor wafer where a circuit pattern is formed, by discriminating the foreign material from a circuit pattern, Japanese Patent Application Laid-Open No. Hei 3-102248 (prior art 1) and Japanese Patent Application Laid-Open No. Hei 3-102249 (prior art 2) are known. To be more specific, in the prior arts 1 and 2, the following are described: a first photoelectric conversion element detects a foreign material on a semiconductor substrate by emphasizing the foreign material using oblique illumination; in addition to it, a second photoelectric conversion element detects the foreign material by emphasizing an edge of a circuit pattern, which is a background on the semiconductor substrate, using incident (vertical) illumination; after that, a foreign material detection signal obtained from the first photoelectric conversion element is divided (or is processed by other operation) by a detection signal obtained from the second photoelectric conversion element; and then, the foreign material is detected by emphasizing the foreign material detection signal.

In addition, as a prior art that separates a foreign material adhering to a surface of a silicon wafer from a crystal defect existing on the surface in order to inspect them, Japanese Patent Application Laid-Open No. Hei 9-304289 (prior art 3) is known. To be more specific, in the prior art 3, the following are described: a low-angle light receiving system, of which an elevation angle with reference to a surface of a silicon wafer is 30° or less, and a high-angle light receiving system having an elevation angle higher than this are provided; the low-angle light receiving system and the high-angle light receiving system receive scattered light, which is obtained by irradiating with a laser beam the surface of the silicon wafer substantially perpendicularly; and a foreign material and a crystal defect are inspected by discriminating the scattered received only by the high-angle light receiving system, which is treated as a crystal defect, from the scattered received by both the low-angle light receiving system and the high-angle light receiving system, which is treated as an adhered foreign material.

Moreover, as a prior art that discriminates a foreign material and a flaw existing on a surface of a semiconductor wafer from a minute dotty concave portion, which will not cause a failure when producing a circuit pattern, without misidentification in order to inspect them, Japanese Patent Application Laid-Open No. Hei 11-142127 (prior art 4) is known. To be more specific, in the prior art 4, the following are described: each of two pieces of illumination light having a wavelength different from each other is condensed and irradiated at the same point on a surface of a semiconductor wafer using a low incident angle and a high incident angle (each of the angles is different from each other); each scattered light from the condense point is received and photoelectric-converted separately according to each of the two wavelengths; and utilizing intensity difference between signals (that is to say, utilizing the fact that from a dotty concave portion, scattered light intensity of illumination light having a low incident angle is weakened), a foreign material and a flaw existing on the surface of the semiconductor wafer are inspected by discriminating the foreign material and the flaw from the dotty concave portion.

By the way, as typical planarization fabrication technique that is used for an object to be fabricated (for example, an insulating layer) at the time of semiconductor production and magnetic head production, there is CMP (Chemical Mechanical Polishing). The CMP is a planarization technology that scatters free abrasive such as silica on a polishing pad, and that polishes a surface of the object to be fabricated. Moreover, as the planarization fabrication technique, grinding fabrication technique may also be used. The grinding fabrication technique buries a fixed abrasive such as a diamond in a polishing pad to perform grinding fabrication in a similar manner. In the polishing or the grinding fabrication technique, on the surface of the object to be fabricated (for example, insulating layer on the semiconductor substrate (wafer)) after polishing or grinding, a scratch showing shape variations, which is a polishing or a grinding flaw, may be produced. In this manner, if a scratch showing shape variations is produced on the surface of the object to be fabricated in the semiconductor production and the magnetic head production, etching will become insufficient in wiring formed on the scratch, which causes a failure such as short circuit. For this reason, it is necessary to observe a wafer polished surface or a ground surface after polishing or grinding and to monitor a state in which a scratch showing shape variations has been produced. If many scratches have been produced, polishing or grinding conditions should be reviewed so that the conditions correspond to the shapes of the scratches. In addition to it, at the same time, if a foreign material adheres, a failure such as an insulation failure or a short circuit of wiring formed on it is caused. If many foreign materials adhere, measures such as equipment scrubbing, which are different from those against a scratch, become necessary. More specifically, in a polishing process or a grinding process for the object to be fabricated (for example, the insulating layer on the semiconductor substrate), a foreign material and a scratch showing shape variations are separately monitored, and appropriate measures are required to be taken against each.

However, all of the prior arts from 1 to 4 did not take the following point into consideration: when the polishing process or the grinding process is performed for the object to be fabricated (for example, the insulating layer on the semiconductor substrate), a scratch showing shape variations, which is produced on the surface, and an adhered particulate foreign material, are inspected while discriminating between them.

Moreover, as regards a size of the scratch showing shape variations, a width W ranges from 0.2 to 0.4 μm approximately, and a depth D ranges from about several nm to about 100 nm (even a very deep scratch), which is very minute. Therefore, an operator conventionally performed visual inspection for review using an electron microscope to discriminate between a scratch showing shape variations and a foreign material, which required a long review time. As a result, measures against a scratch or a particulate foreign material are delayed, which causes a large quantity of wafers to be polished continuously in bad conditions, resulting in a great loss in profit.

SUMMARY OF THE INVENTION

An object of the present invention is to provide a defect-inspecting apparatus and its method, by which for the purpose of solving the problems, a scratch, etc. showing shape variations, which are produced on the surface, are discriminated from an adhered particulate foreign material to inspect them when the polishing process or the grinding process, such as CMP, is performed for an object to be fabricated (for example, an insulating layer on a semiconductor substrate) in semiconductor production and magnetic head production.

In addition, another object of the present invention is to provide a method for producing a semiconductor substrate, by which a semiconductor substrate free from a defect can be produced with high reliability and high efficiency by enabling hundred percent inspection or random inspection with sufficient frequency so that a scratch, etc. showing shape variations, which are produced on the surface, are discriminated from an adhered particulate foreign material to inspect them when the polishing process or the grinding process, such as CMP, is performed for an object to be fabricated (for example, an insulating layer on a semiconductor substrate).

In addition, another object of the present invention is to provide a method for producing a semiconductor substrate, by which a semiconductor substrate free from a defect can be produced with high reliability and high efficiency by enabling discrimination of a concave defect such as a thin film-like foreign material and a scratch, which has a low height and a shallow depth, from a convex defect such as a particulate foreign material, which has a high height, to inspect the defects.

In order to achieve the objects described above, the present invention provides a defect-inspecting apparatus and method comprising:
  a stage on which an object to be inspected is mounted;
  an illumination optical system comprising;
    an incident illumination system which incident-illuminates illumination light including UV light or DUV light at a point on a surface of the object to be inspected, which is mounted on the stage, with desired luminous flux from a normal line direction relative to the surface or from a direction in proximity to the normal line; and
    a oblique illumination system which oblique-illuminates illumination light including UV light or DUV light at a point on the surface of the object to be inspected with desired luminous flux;
  a detection optical system comprising;
    a high-angle image formation optical system which condenses first high-angle scattered light traveling at a high angle relative to the surface of the object to be inspected, from among first reflection light generated from the point, which has been incident-illuminated by the incident illumination system of the illumination optical system, and second high-angle scattered light traveling at the high angle, from among second reflection light generated from the point, which has been oblique-illuminated by the oblique illumination system of the illumination optical system, in order to perform image formation; and
    a photoelectric conversion unit which receives the first and the second high-angle scattered light, of which image formation has been performed in the high-angle image formation optical system, to convert the first and the second high-angle scattered light into a first and a second luminance signal (S(i), T(i)); and
    a comparison and judgment unit which classifies defects i on the object to be inspected into concave defects and convex defects on the basis of a correlation between the first luminance signal S(i) and the second luminance signal T(i), which have been converted by the photoelectric conversion means of the detection optical system.

In addition, the present invention is characterized by the following:
  the incident illumination system of the illumination optical system in the defect-inspecting apparatus is configured to irradiate the surface of the object to be inspected with incident illumination light without irradiating a condenser lens so that stray light is not generated from the high-angle condensation optical system.

In addition, the present invention is characterized by the following:
  the detection optical system in the defect-inspecting apparatus additionally comprises a shielding unit (element) which shields a specific light image, which is caused by the first reflection light, on a Fourier transformed surface of the first reflection light emitted from the point.

In addition, the present invention is characterized by the following:
  in the comparison and judgment unit in the defect-inspecting apparatus, ratios (T(i)/S(i), S(i)/T(i)) are used as the correlation.

In addition, the present invention is characterized by the following:
  the comparison and judgment unit in the defect-inspecting apparatus is configured to classify concave defects into scratches and thin film-like foreign materials (because a thickness of the thin film-like foreign material is very thin, it is defined as a concave defect in the present invention) on the basis of data in response to a defect size calculated by the first luminance signal S(i) and the second luminance signal T(i).

In addition, the present invention is characterized by the following:
  the comparison and judgment unit in the defect-inspecting apparatus is configured to classify particulate foreign materials, which are a convex defect, into a small group and a large group on the basis of data in response to a defect size calculated by the first luminance signal S (i) and the second luminance signal T(i).

In addition, the present invention is characterized by the following:
  the comparison and judgment unit in the defect-inspecting apparatus is configured to judge that the classified convex defect occurs inside a circuit pattern area, or that the classified convex detect occurs outside the circuit pattern area.

In addition, the present invention is characterized by the following:
  the comparison and judgment unit in the defect-inspecting apparatus has a displaying unit for displaying information of a discriminated defect.

In addition, the present invention is characterized by the following:

the comparison and judgment unit in the defect-inspecting apparatus has a displaying unit for displaying information about a relation of the first luminance signal to discriminate a defect.

In addition, the present invention is characterized by the following:

the comparison and judgment unit in the defect-inspecting apparatus has a displaying unit for displaying information about a relation of the second luminance signal to discriminate a defect.

In addition, the present invention is characterized by the following:

the comparison and judgment unit in the defect-inspecting apparatus has a displaying unit for plotting a relation between the first luminance signal and the second luminance signal, which have been converted by the photoelectric conversion unit of the detection optical system, on a correlation diagram, where a horizontal axis and a vertical axis are expressed by logarithm values, to display the relation.

In addition, the present invention is characterized by the following:

in the illumination optical system in the defect-inspecting apparatus, a point incident-illuminated by the incident illumination system and a point oblique-illuminated by the oblique illumination system, which are on the surface of the object to be inspected, are configured to be different from each other in a visual field of the detection optical system.

Moreover, the present invention provides a defect-inspecting apparatus and method comprising:

a stage on which an object to be inspected is mounted;
an illumination optical system comprising;
  an incident illumination system that incident-illuminates illumination light including UV light or DUV light at a point on a surface of the object to be inspected, which is mounted on the stage, with desired luminous flux from a normal line direction relative to the surface or from a direction in proximity to the normal line; and
  a oblique illumination system that oblique-illuminates illumination light including UV light or DUV light, which has a wavelength different from that of said incident-illuminated illumination light, at a point on the surface of the object to be inspected with desired luminous flux;
a detection optical system comprising;
  a condensing optical system which condenses first high-angle scattered light traveling at a high angle relative to the surface of the object to be inspected, from among first reflection light generated from the point, which has been incident-illuminated by the incident illumination system of the illumination optical system, and second high-angle scattered light traveling at the high angle, from among second reflection light generated from the point, which has been oblique-illuminated by the oblique illumination system of the illumination optical system; and
  a wavelength separation optical system which wavelength-separates the first high-angle scattered light and the second high-angle scattered light, which have been condensed by the condensing optical system;
  an image formation optical system which performs image formation of each of the first high-angle scattered light and the second high-angle scattered light, which have been separated by the wavelength separation optical system; and
  a first and a second photoelectric conversion unit which receives each of the first high-angle scattered light and the second high-angle scattered light, for which image formation has been performed by the image formation optical system, to convert the first high-angle scattered light and the second high-angle scattered light into a first luminance signal and a second luminance signal respectively; and
a comparison and judgment unit which discriminates a defect on the object to be inspected on the basis of a relation between the first luminance signal converted by the first photoelectric conversion means and the second luminance signal converted by the second photoelectric conversion means in the detection optical system.

In addition, the present invention provides a defect-inspecting method comprising the steps of:

incident-illuminating and oblique-illuminating illumination light including UV light or DUV light on a shallow scratch and a foreign material, which are made on a surface of a polished or a ground film, with substantially the same luminous flux;

receiving scattered light caused by a shallow scratch and a foreign material, which is generated by the incident illumination and the oblique illumination, by a detector to convert the scattered light into luminance signals in response to each intensity of the scattered light; and discriminating between the foreign material and the shallow scratch on the basis of a correlation of the converted luminance signals.

In addition, the present invention provides a defect-inspecting method comprising the steps of:

incident-illuminating and oblique-illuminating illumination light including UV light or DUV light on a flat thin film-like foreign material and a foreign material, which are made on a surface of a polished, washed, or a sputtered film, with substantially the same luminous flux;

receiving scattered light caused by a thin film-like foreign material and a foreign material, which is generated by the incident illumination and the oblique illumination, by a detector to convert the scattered light into a luminance signals in response to each intensity of the scattered light; and discriminating between the thin film-like foreign material and the foreign material on the basis of a correlation of the converted luminance signals.

BRIEF DESCRIPTION OF THE DRAWING

FIG. 4 is a diagram illustrating principles of discrimination between a scratch and a particulate foreign material, according to the present invention;

DETAILED DESCRIPTION OF THE PREFERRED EMBODIMENTS

Embodiments of a defect-inspecting apparatus and method according to the present invention, which are used in a semiconductor production process or a magnetic head production process, and which aim to operate a planarization fabrication process with stability, will be described with reference to drawings as below.

Figure 1:
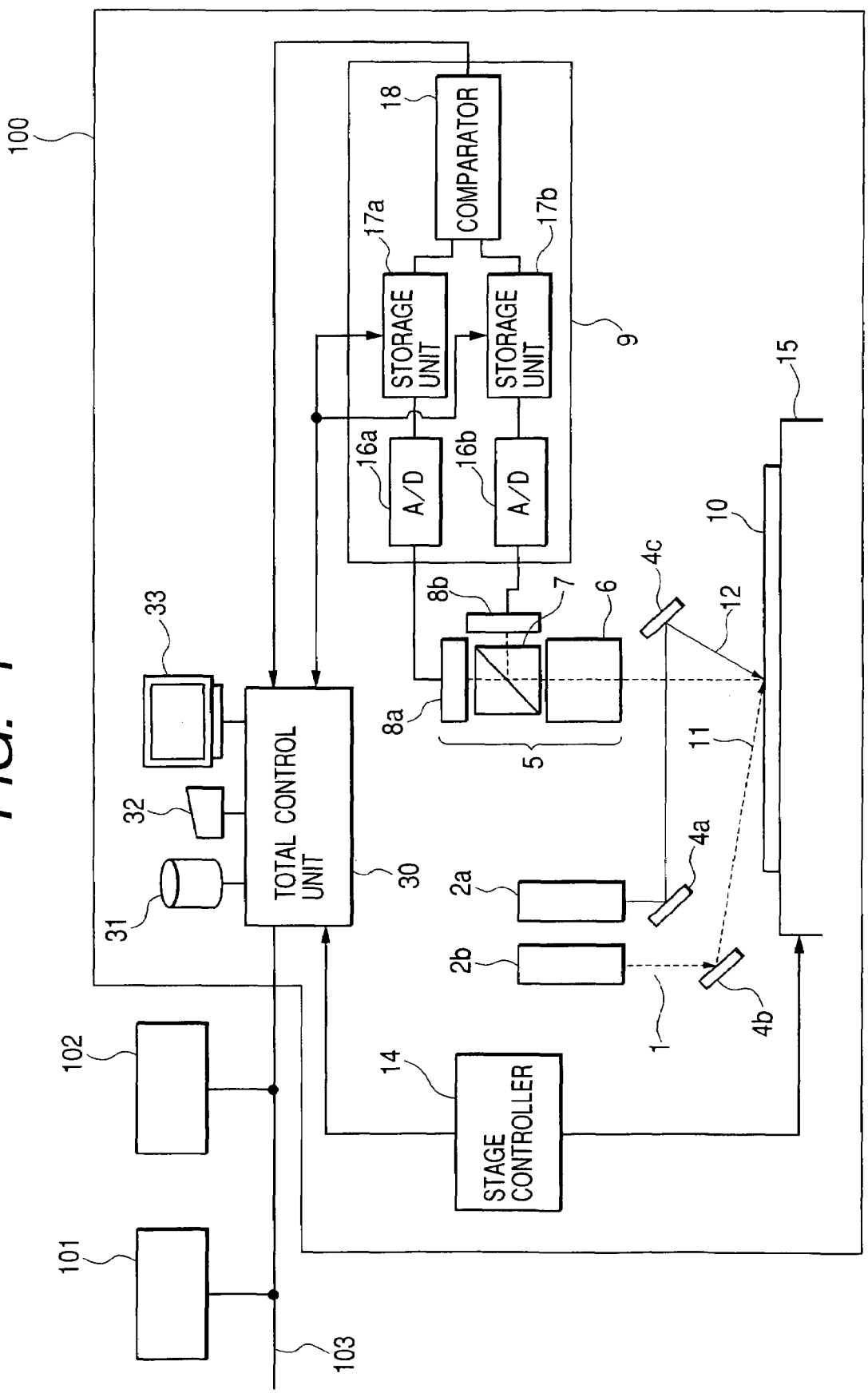
FIG. 1 is a schematic configuration diagram illustrating a first embodiment of a defect-inspecting apparatus according to the present invention.

In the first place, a first embodiment of the defect-inspecting apparatus and its method according to the present invention will be described. As shown in FIG. 1, the present invention relates to a defect-inspecting apparatus 100 that performs sampling inspection or hundred-percent inspection of products in the middle of a semiconductor production process. As regards a semiconductor production line, a process-control computer 101 manages production conditions, for example, through a network 103, or for each individual production equipment (not illustrated). In the middle of the process, a semiconductor is inspected using a foreign-material inspecting apparatus, an optical visual inspecting apparatus, a SEM inspecting apparatus, or by humans. If an abnormal condition is found as a result of the inspection, review is performed using an optical reviewing apparatus, a SEM reviewing apparatus, or the like. As occasion requires, more detailed analysis is performed using EDX (Energy Dispersive X-ray Spectroscopy), etc. to identify a cause of the abnormal condition. After that, measures for production conditions and production equipment, which have caused the abnormal condition, are taken to improve a yield factor. Moreover, data such as coordinates and sizes of a foreign material and a defect, which have been detected by the defect-inspecting apparatus 100, and additionally, data of kind, category, etc. of defects, which are discriminated (classified), are managed online by a yield-factor managing system 102.

Figure 2A:
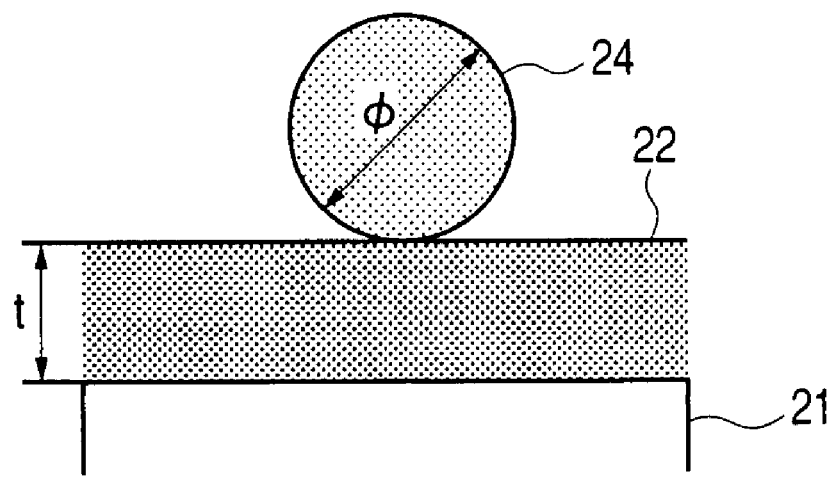
FIGS. 2(a) and 2(b) are diagrams illustrating shape parameters of a scratch and a foreign material, which are made on an insulating layer by CMP, according to the present invention.
Figure 2B:
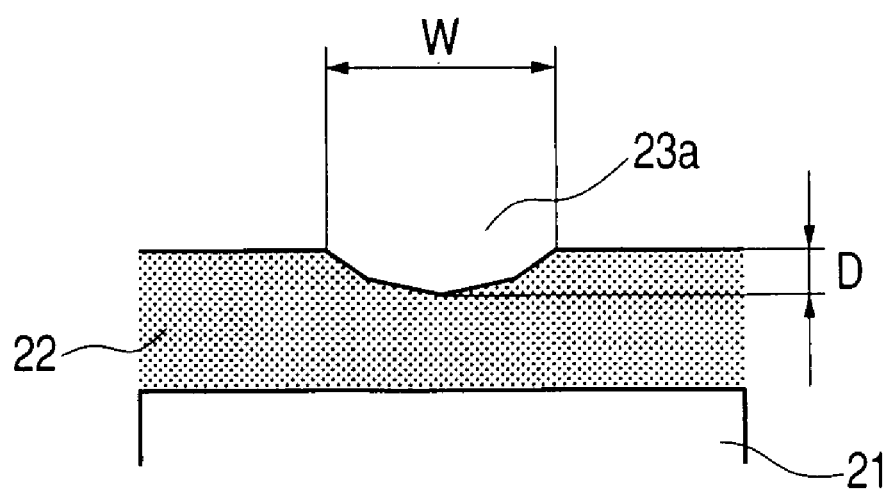
Figure 3A:
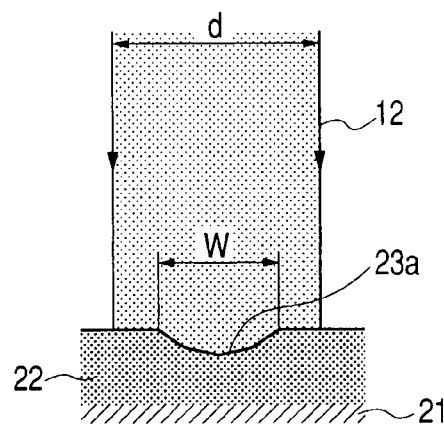
FIGS. 3(a) through 3(d) are diagrams for describing a length of projected incidence light when irradiating a scratch and a foreign material with luminous flux d, according to the present invention.
Figure 3B:
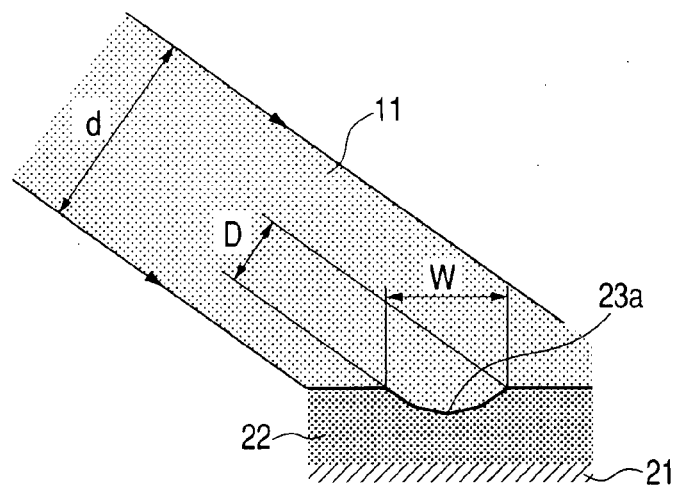
Figure 3C:
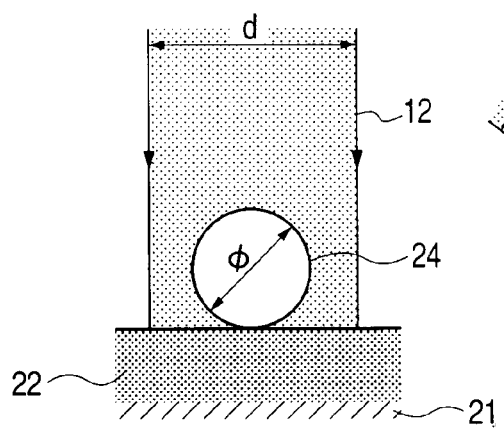
Figure 3D:
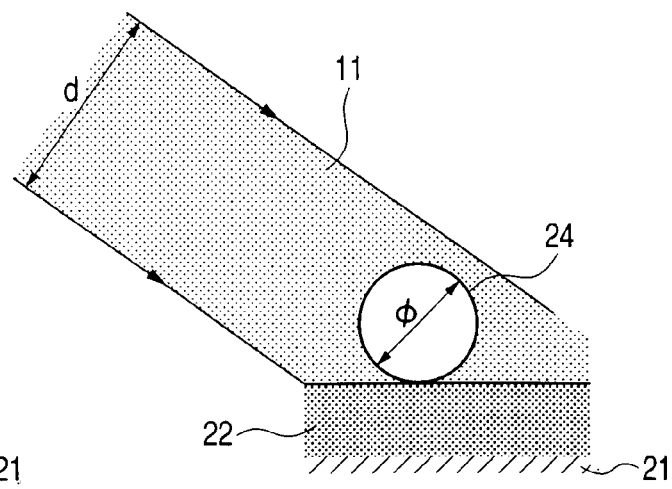

As shown in FIG. 2, the defect-inspecting apparatus 100 according to the present invention is characterized by the following: forming an interlayer insulating layer (an object to be fabricated) 22 of a $SiO_2$ film, etc. on a Si wafer 21; and when performing CMP (Chemical Mechanical Polishing), discriminating a foreign material 24 from a shallow scratch 23a that has been made on a wafer 10. It is to be noted that the semiconductor substrate 21 of Si substrates, etc. is not always provided under the interlayer insulating layer 22 of the $SiO_2$ film, etc. A wiring layer may also be provided. In the CMP process, a surface of the $SiO_2$ film 22 is polished for planarization. Because of it, the scratch 23a, which is a flaw caused by polishing, is produced on the surface of the $SiO_2$ film 22 as shown in FIG. 2(b). In this case, a film thickness of the $SiO_2$ film 22 is t; a width of the scratch 23a is W; and a depth is D. As an approximate size of the scratch 23a, W approximately ranges from 0.2 to 0.4 μm. In addition, the depth D approximately ranges from several nm to 100 nm (even if it is very deep). Thus, the scratch 23a, which is made in CMP, is characterized in that a depth is very shallow relative to a width. FIG. 2(a) shows dimension parameters of the foreign material 24. In this case, the foreign material 24 is modeled as a particulate matter with a diameter Φ. The real foreign material 24 does not have such a regular spherical shape. However, it is found out that concerning the scratch 23a, the depth D is very shallow (approximately ranging from several nm to several tens nm) relative to the width W (approximately ranging from 0.2 to 0.4 μm), and that concerning the foreign material (particulate foreign material) 24, there is not extreme large difference between a width and a height as compared with the scratch 23a. The present invention pays attention to the ratio of dimensions peculiar to the scratch 23a.

Next, a first example of a surface inspecting apparatus for inspecting scratches, which is used to realize the first embodiment, will be described with reference to FIGS. 1 through 9. To be more specific, as shown in FIG. 1, the first example of the surface inspecting apparatus comprises a stage 15, an illumination optical system 1, a detection optical system 5, an operation processing unit 9, a stage controller 14, and a total control unit 30. Movements of the stage 15 in X and Y direction are controlled while position coordinates of the stage 15 are measured, and a wafer 10 as an object to be inspected is mounted on the stage 15. The illumination optical system 1 includes for example a plurality of light sources 2a, 2b, each of which outputs light having a wavelength different from each other, and which include light sources (not limited to a laser beam source) such as Ar laser light having a wavelength of 488 nm (a wavelength of blue), nitrogen laser light, He—Cd laser light, and excimer laser light, and reflection mirrors 4a, 4b, 4c. The detection optical system 5 includes a condenser lens 6, a beam splitter 7 for splitting light according to a wavelength, and photoelectric converters 8a, 8b comprising a photo-multiplier, a CCD camera, a CCD sensor, and a TDI sensor. The operation processing unit 9 includes A/D converters 16a, 16b for converting an analog luminance signal, which is output from each of the photoelectric converters 8a, 8b, into a digital luminance signal, storage units 17a, 17b for temporarily storing a digital luminance signal obtained from each of the A/D converters 16a, 16b, and a comparator 18. The stage controller 14 controls movement of the stage 15 on the basis of position coordinates of the stage 15 measured by a laser displacement meter (not shown). A total control unit 30 controls the stage controller 14 before controlling the operation processing unit 9, and that receives an inspection result obtained from the operation processing unit 9.

As light sources 2a, 2b, it is desirable to use a light source, of which a wavelength is as short as possible, such as an excimer laser light source in order to detect the minute foreign material 24 and the minute scratch 23, which are made on the insulating layer 22 processed by CMP, while discriminating them. To be more specific, as the light source 2a, it is possible to use a laser beam source that outputs a laser beam having a wavelength of 488 nm or 365 nm for example; and as the light source 2b, it is possible to use a laser beam source that outputs a DUV laser beam or KrF excimer laser light, which has a wavelength twice as long as a YAG laser wavelength (532 nm) or a wavelength four times as long as the YAG laser wavelength (266 nm). A wafer surface (a surface of the insulating layer processed by CMP) is irradiated with the UV light or the DUV light emitted from the light source 2a from a normal line (vertical) direction or its proximity, through the reflection mirrors 4a and 4c, without irradiating directly on a surface of the condenser lens 6. This is called incident illumination 12. Or the wafer surface (a surface of the insulating layer processed by CMP) is irradiated with the UV light or the DUV light emitted from the light source 2b from a oblique direction through the reflection mirror 4b. This is called oblique illumination 11. In the first example, incident illumination and oblique illumination are realized using two light sources 2a, 2b, which are separated from each other, and a plurality of reflection mirrors 4a through 4c. However, the following configuration may also be used: one light source 2b; and an optical-path switching mechanism (not shown) for switching an optical path of the UV light or the DUV light, which is emitted from the light source 2b, to the mirror 4b and the mirror 4c. In addition, the example can be configured regardless of the number of reflection mirrors, and existence of the optical-path switching mechanism.

Moreover, a wavelength of the incident illumination light 12 can conform to that of the oblique illumination light 11 by configuring the illumination optical system 1 so that a point on a wafer surface, at which incident illumination light 12 is incident-illuminated in an incident illumination system, is differentiated from a point on the wafer surface, at which oblique illumination light 11 is oblique-illuminated in a oblique illumination system, within a visual field of detection optical system 5. However, in this case, it is necessary to place light receiving surfaces for the photoelectric converter 8a and the photoelectric converter 8b so that each of the light receiving surfaces corresponds to difference between the irradiation points on the wafer surface.

In this manner, the illumination optical system 1 only requires that illumination (incident illumination and oblique illumination) 11, 12 using two routes are realized without irradiating directly a surface of the condenser lens 6; that is to say, one route is from a normal line direction (or from a direction of its proximity) relative to a CMP surface where CMP is processed for the insulating layer 22 on the wafer 10, and another route is from a oblique direction near from a wafer horizontal plane (an angle of 30° or less). In the case of the incident illumination 11, as shown in FIG. 1, it may be pseudo incident illumination that is as near a vertical direction as possible.

Next, detection procedures will be described. Detection is performed twice for one piece of the wafer 10 while switching an illumination direction. More specifically, in the first place, a CMP surface of the insulating layer 22 on the wafer 10 is irradiated with incident illumination light 12 including UV light or DUV light, which is emitted by the light source 2a, without irradiating directly on a surface of the condenser lens 6. Then, without generating stray light, which is reflected from minute surface roughness of a surface of the condenser lens 6 and from very minute foreign materials adhering to the surface, and in a state in which regular reflection light component generated from the insulating layer 22 is removed, only scattered light (a low order diffraction light component), which is emitted from the extremely shallow and minute scratch 23a and the foreign material 24 made on the insulating layer 22 by CMP, is condensed by the condenser lens 6. After that, through the beam splitter 7, the condensed light is received on a light receiving surface of the photoelectric converter 8a comprising for example CCD and TDI sensors. Then, an output of the photoelectric converter 8a is analog-to-digital converted by the A/D converter 16a to acquire a luminance value S(i) for each defect i before the output is written to the storage unit 17a temporarily.

At the same time, the same coordinate position as that of the incident illumination light 12 on the wafer surface oblique is irradiated with illumination light 11 including UV light or DUV light, which is emitted from the light source 2b, and which has a wavelength different from that of the light source 2a.

By the way, the total control unit 30 may control movement of the stage 15, which switches the irradiation direction using the optical-path switching mechanism (not shown) so that the oblique illumination light 11 is irradiated for the same position coordinate system as that of the incident illumination light 12 on the wafer surface.

Then, in a state in which regular reflection light component generated from the insulating layer 22 is removed, only scattered light (a low order diffraction light component) emitted from the extremely shallow and minute scratch 23a and the foreign material (particulate foreign material) 24, which have been made by CMP on the insulating layer 22, is condensed by the condenser lens 6. After that, through the beam splitter 7, the condensed light is received by the photoelectric converter 7b for example. Then, an output of the photoelectric converter 7b is analog-to-digital converted by the A/D converter 16b to acquire a luminance value T(i) for each defect i before the output is written to the storage unit 17b temporarily.

Next, the comparator 18 calculates a ratio R(i) of the detected luminance value S(i) for each defect i obtained by the incident illumination 12, which is stored in the storage unit 17a, to the detected luminance value T (i) for each defect i obtained by the oblique illumination 11, which is stored in storage unit 17b. If the calculated luminance ratio R(i) is higher than a predetermined threshold value (reference value for judgment: the discrimination line 20 shown in FIG. 5), the comparator 18 judges it to be the foreign material 24. If the luminance ratio R(i) is lower, the comparator 18 judges it to be the extremely shallow and minute scratch 23a. After the judgment, the comparator 18 outputs the result to the total control unit 9. In this manner, the scratch 23a made by CMP is extremely shallow and minute. Therefore, if the incident illumination light 12 is irradiated on the surface of the condenser lens 6, feeble stray light generated from the surface of the condenser lens 6 will be also received by, for example, the photoelectric converter 7a. In this case, it becomes difficult to discriminate the stray light from the scattered light from the scratch 23a. For this reason, the apparatus in the example is configured so that the surface of the condenser lens 6 is not irradiated with the incident illumination light 12.

In the first example, detection by the incident illumination light 12 and detection by the oblique illumination light 11 are performed simultaneously. However, it is to be noted that the detection by the incident illumination light 12 may be performed first before the detection by the oblique illumination 11 later, and that the detection by the oblique illumination light 11 may be performed first before the detection by the incident illumination light 12. In addition, as regards the first example, the present invention can also be realized by the following: writing a detected luminance value T(i) by the oblique illumination 11, which is the second detection, to the storage unit 17 temporarily after A/D conversion; without storing the second detected luminance value T(i), referring to a detected luminance value S(i) by the first incident illumination 12, which has already been stored concurrently with the detection, in the comparator 18; and then performing luminance comparison operation.

Next, discrimination principles for realizing the embodiment according to the present invention will be described with reference to FIGS. 3 and 4 in detail. In the present invention, discrimination is performed by irradiating one defect with luminous flux d from two different angles (for example, the incident illumination 12 and the oblique illumination 11). In the first place, as the incident illumination light 12, the defect is irradiated with luminous flux d from a normal line direction of the wafer surface or from its proximity without irradiating the surface of the condenser lens 6 directly. Next, as the oblique illumination light 11, the wafer surface is irradiated with luminous flux d from an angle near from a horizontal direction. The incident illumination 12 and the oblique illumination 11 may be performed regardless of the order of illumination operation. The discrimination is performed by comparing intensity of scattered light emitted from the defects 23a, 24; in this case, each intensity is obtained by each of the illumination from the two directions with luminous flux d. Intensity of the scattered light emitted from the defects 23a, 24 is determined in response to light quantity of the light source, from which the defects 23a, 24 have received light. As shown in FIG. 3, it may be considered that the light quantity of light source, from which the defects 23a, 24 receive light, is substantially proportional to a projected area of a defect size in a light source incident direction.

In the case of the scratch 23a that is a concave defect, this projected area is substantially proportional to a width W at the time of the incident illumination. On the other hand, at the time of the oblique illumination irradiated at a shallow angle of about 30° or less, the projected area is substantially proportional to D'. On the contrary, the depth D of the scratch 23a is very shallow as compared with the width W. Therefore, this oblique illumination projected length D' becomes very short as compared with an incident illumination projected length W'. As a result, light quantity of scattered light emitted from the scratch 23a at the time of the oblique illumination 11 is weaker. As compared with this, in the case of the foreign material (particulate foreign material) 24 that is a convex defect, projected lengths Φ of the oblique illumination 11 and the incident illumination 12 are substantially the same. Therefore, light quantity of scattered light emitted from the foreign material 24 does not indicate great change even if the oblique illumination and the incident illumination are compared. For this reason, as shown in FIG. 4, the following judgment becomes possible: detected luminance values S(i), T(i) of scattered light by the incident illumination 12 and the oblique illumination 11 are compared with each other; if the oblique illumination 11 is smaller than the incident illumination 12, it is judged to be the scratch 23a; and if the oblique illumination 11 is larger than or equal to the incident illumination, it is judged to be the foreign material (particulate foreign material) 24.

Moreover, a thickness of the thin film-like foreign material 23b is also very thin. Because of it, as is the case with the scratch 23a, a detected luminance value T(i) of the scattered light by the oblique illumination 11 is smaller than a detected luminance value S(i) of the scattered light by the incident illumination 12, which allows us to consider the thin film-like foreign material 23b to be a concave defect.

Figure 5:
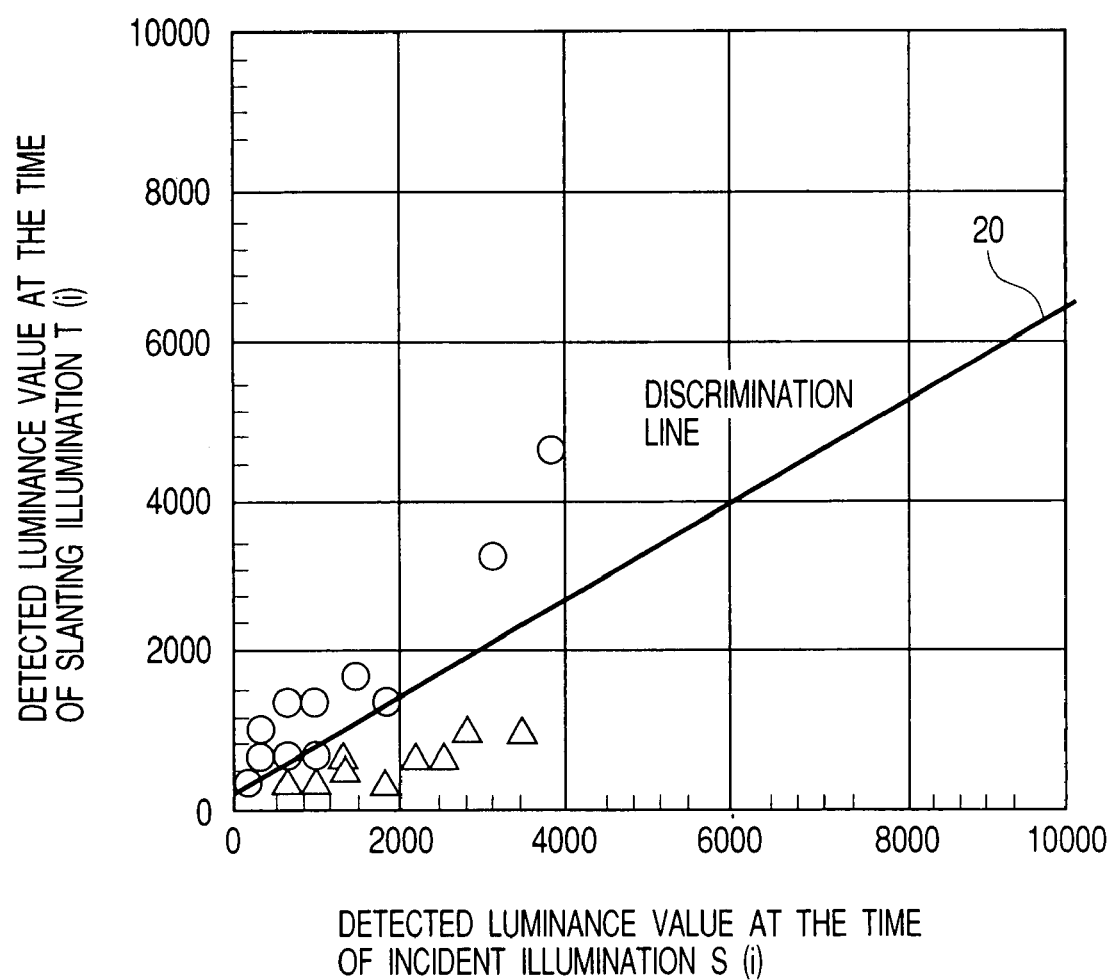
FIG. 5 is a diagram illustrating one example of principles of discrimination between a scratch and a particulate foreign material, according to the present invention.

FIG. 5 is a graph illustrating an example of this discrimination result. This is a graph in which a horizontal axis is used for the detected luminance value S (i) at the time of the incident illumination, and a vertical axis is used for the detected luminance value T (i) at the time of the oblique illumination. In this case, an area below a discrimination line 20 shown in the figure is an area of the scratch 23a, and an area above the discrimination line 20 is an area of the foreign material 24. However, in reality, as shown in FIG. 5 clearly, even if the detected luminance value S(i) at the time of the incident illumination and the detected luminance value T (i) at the time of the oblique illumination are simply compared to calculate a ratio between them, it is not possible to draw (determine) a discrimination line (threshold value for judgment) 20. This means that it is difficult to discriminate between the foreign material 24 and the scratch 23a. Therefore, an example of a method for discriminating between the foreign material (particulate foreign material) 24 and the scratch 23a specifically according to the present invention, using the detected luminance value S(i) at the time of the incident illumination and the detected luminance value T(i) at the time of the oblique illumination, will be described later.

By the way, because the insulating layer (for example, $SiO_2$ film) 22, on which the scratch 23a is made by CMP, is transparent to light, regular reflection light from a lower layer, which includes light interference, is generated. However, in the case of the incident illumination 12 in particular, as shown in FIG. 1, it is necessary to devise the following method: for example, placing the reflection mirror 4c outside a visual field of the condenser lens 6, which causes regular reflection light (including light interference light) from a surface of the insulating layer 22 and its lower layer to go out of a visual field of the condenser lens (object lens) 6 so that, for example, the photoelectric converter 8a does not detect the regular reflection light.

As a matter of course, in the case of the oblique illumination 11, as shown in FIG. 1, the oblique illumination 11 is irradiated at a very shallow angle by the reflection mirror 4b. Therefore, the regular reflection light (including light interference light) from the surface of the insulating layer 22 and its lower layer goes out of a visual field of the condenser lens 6. As a result, the regular reflection light is not detected by the photoelectric converter 8b.

Additionally, if a light source, which emits broadband light or white light, is used as the light source 2, a problem of light interference between regular reflection light from the surface of the insulating layer 22 and regular reflection light from the lower layer does not arise. However, in order to obtain scattered light having high intensity from the minute scratch 23a (depth D is shallow in particular) and the foreign material 24 on the insulating layer 22, it is desirable to use UV light or DUV light as illumination light.

Next, an example of a method for installing the reflection mirror 4c will be described with reference to FIG. 6. This is a method for preventing stray light of a dark-field detecting system to detect a defect with high sensitivity. As it can be understood from the principles described above, the inspection of the scratch 23a requires illumination from a direction that is near from a normal line relative to a surface of the wafer 10.

However, as regards incident illumination of UV light or DUV light, when incident illumination light is illuminated on the wafer 10 through the condenser lens 6, so-called stray light is produced, which causes a noise in a detected image. More specifically, it is because scattered light, which is made by a minute scar caused by polishing on the surface of the condenser lens 6 or is made by dust adhering to the condenser lens 6, becomes stray light. Because of it, when receiving minute scattered light from the defects 23a, 24 using the photoelectric converter 8a to observe the scattered light, the stray light becomes fatal. To be more specific, the scattered light from the extremely small scratch 23a is hidden in noise caused by the stray light, which hinders detection of the scattered light.

For this reason, in the present invention, as shown in FIG. 6, it is necessary to provide a reflection mirror 4c so that the surface of the condenser lens 6 is not irradiated with incident light having high intensity, and so that zero-order diffraction light, which is a regular reflection light component (including coherent light component) from the wafer 10 (a surface (CMP surface) of the interlayer insulating layer 22, a surface of its lower wiring layer, a surface of the scratch 23a, and a surface of the foreign material 24) does not enter the condenser lens 6 (that is to say, inside NA).

Figure 6A:
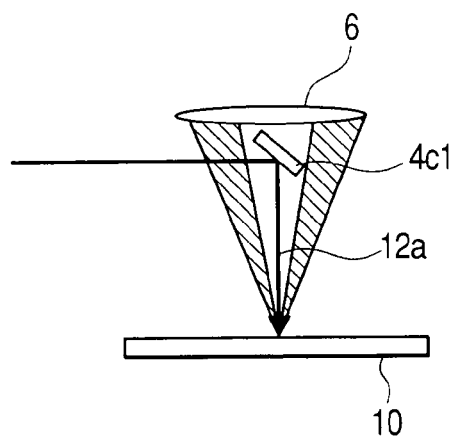
FIGS. 6(a) through 6(d) are diagrams illustrating an example of vertical irradiation and pseudo vertical illumination according to the present invention.

FIG. 6(a) shows a means comprising the steps of: placing the small reflection mirror 4c1 substantially on a normal line of the wafer 10, which is between the wafer 10 and the condenser lens 6; throwing the incident illumination light 12a on the small reflection mirror 4c1 from a lateral direction to reflect the incident illumination light 12a so that the surface of the condenser lens 6 is not irradiated; in addition to it, reflecting a regular reflection light component (including a coherent light component) from the wafer 10 by the reflection mirror 4c1 so that the regular reflection light component is not thrown into a pupil of the condenser lens 6; and among scattered light (first-order diffraction light component or more) from the scratch 23a and the foreign material 24, throwing scattered light (low order diffraction light component) of an area shown by oblique lines (shaped like a circular zone if it is viewed as a plane) into the pupil of the condenser lens 6. It is to be noted that an outside shape of this small reflection mirror 4c1 is substantially oval. This is called scattered light detection by vertical illumination. However, this means is not so desirable because a role as a lens is lost in a center portion of the condenser lens 6.

Figure 6B:
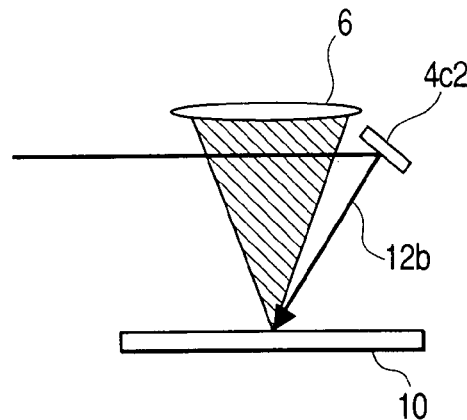

In addition, FIG. 6(b) shows a means comprising the steps of: placing the reflection mirror 4c2 outside NA of the condenser lens 6, and between the wafer 10 and the condenser lens 6; throwing the incident illumination light 12b on the reflection mirror 4c2 from a lateral direction to reflect the incident illumination light 12b so that the surface of the condenser lens 6 is not irradiated; leading a regular reflection light component from the wafer 10 to outside of the pupil of the condenser lens 6; and from among scattered light from the scratch 23a and the foreign material 24, throwing scattered light of an area, which is shown by oblique lines, into the pupil of the condenser lens 6. It is to be noted that, if the reflection mirror 4c2 is extended in a circumferential direction, illumination light, which is illuminated by the reflection mirror 4c2, assumes circular zone illumination. In this case, for example, providing three reflection mirrors 4c2 at intervals of 120 degrees in a circumferential direction, and throwing each of three illumination light 12b, which is obtained from between those three reflection mirrors 4c2 respectively, enable circular zone illumination from three directions. On the contrary, as shown in FIG. 6(b), if the reflection mirror 4c2 is made partial, it assumes partial illumination of circular zone illumination. There are called scattered light detection by pseudo vertical illumination. This means is very effective because the whole visual field (pupil) of the condenser lens 6 is used. However, it is necessary to add the number of luminous flux of the oblique illumination light 11 to the number of luminous flux of the incident illumination light 12b.

Figure 6C:
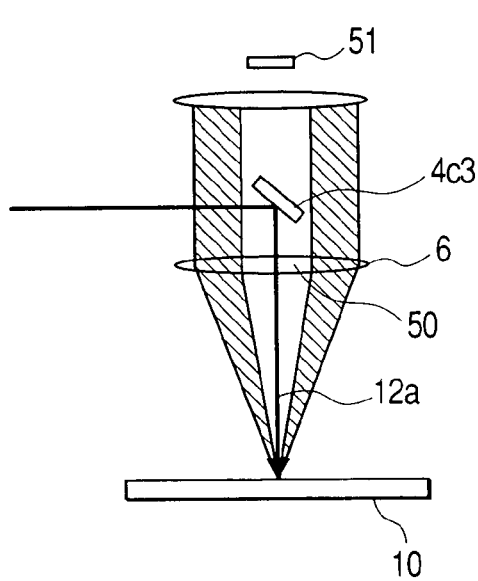

Moreover, FIG. 6(c) shows a means comprising the steps of: placing a small-sized reflection mirror or a small-sized half mirror 4c3 in a proximity to an optical axis above the condenser lens 6; placing the condenser lens 6, through which an opening 50 is bored centrally; irradiating an insulating layer CMP surface on the wafer 10 with the vertical illumination light 12a, which is reflected by the small-sized reflection mirror or the small-sized half mirror 4c3, through the opening 50 without irradiating the surface of the condenser lens 6; shielding a regular reflection light component from the wafer 10 using a spatial filter (shielding element) 51 provided on a Fourier transformed surface; and receiving scattered light, which is obtained through the condenser lens 6 from among scattered light from the scratch 23a and the foreign material 24, by the photoelectric converter 8a.

Figure 6D:
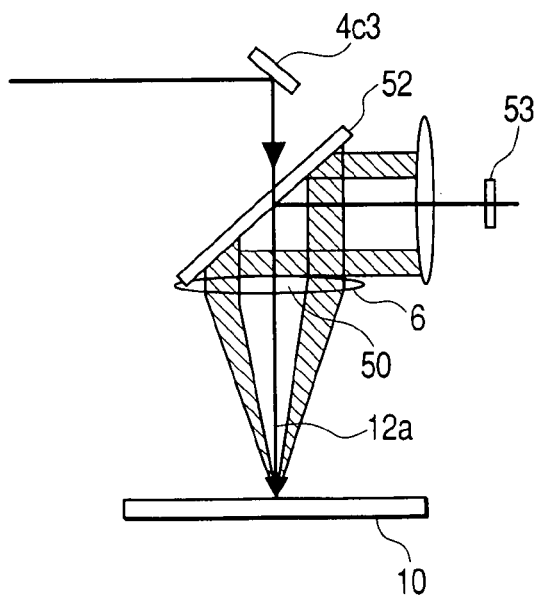

Furthermore, FIG. 6(d) shows a means comprising the steps of: as is the case with FIG. 6(c), transmitting the incident illumination light 12a through a central portion of the half mirror 52 to illuminate the incident illumination light 12a vertically on a CMP surface of the wafer 10 through the opening 50 of the condenser lens 6; shielding regular reflection light from the wafer 10 using the spatial filter (a shielding element) 53 provided on the Fourier transformed surface; reflecting scattered light, which is obtained through the condenser lens 6 from among scattered light from the scratch 23a and the foreign material 24, by a perimeter portion of the half mirror 52; and receiving the scattered light using the photoelectric converter 8a. It is to be noted that a perimeter portion of the half mirror 52 may be configured by a reflection mirror.

As described above, in FIGS. 6(c) and 6(d), as is the case with FIG. 6(a), forming the opening 50 in the center of the condenser lens 6 enables scattered light detection from vertical illumination and a vertical direction without generating stray light from the surface of the condenser lens 6. Because of it, even if the scratch 23a is formed in any direction in a horizontal plane, scattered light, which is generated from an edge of the very shallow scratch 23a, can be received by the photoelectric converter 8a comparatively uniformly, which enables acquirement of uniform detected luminance value S (i). In addition, in order to get diffraction light having strong directivity in a right-angle direction relative to a large scratch (not illustrated), which is a linear pattern, vertical illumination is more desirable than pseudo vertical illumination. However, the examples shown in FIGS. 6(c) and 6(d) are not so desirable because the opening 50 should be formed in the central portion of the condenser lens 6, which causes a function of the condenser lens 6 to be decreased.

By the way, in the case of the scattered light detection by vertical illumination shown in FIG. 6(a), the surface of the condenser lens 6 is not irradiated with incidence light obviously because the incidence light passes below the lens 6. Therefore, stray light is not generated. Additionally, because regular reflection light from the wafer 10 is reflected by the reflection mirror 4c1, the regular reflection light does not enter the pupil of the condenser lens 6. In addition, the vertical illumination shown in FIGS. 6(c) and 6(d) also does not enter the pupil of the condenser lens 6. Moreover, in the case of the scattered light detection by pseudo vertical illumination shown in FIG. 6(b), incidence light is not transmitted through the condenser lens 6 obviously. Furthermore, because the reflection mirror 4c2 is placed outside NA of the condenser lens 6, a regular reflection light component from the wafer 10 does not enter the pupil of the condenser lens 6. To be more specific, in any means, incident illumination is realized so that the incidence light, of which beam intensity is high, and which is prone to generate stray light, does not irradiate the surface of the condenser lens 6, and so that regular reflection light from the wafer is not thrown onto the condenser lens 6. Therefore, acquirement of a detected image having a high S/N ratio becomes possible from the scratch 23a and the foreign material 24 that are made on a CMP surface, which is not prone to generate stray light, and on which CMP has been provided for the interlayer insulating layer 22. By the way, because the interlayer insulating layer 22 is transparent to light, light, which is regularly reflected from a lower layer, returns at the time of incident-illumination. However, as described below, because the light is not thrown into NA of the condenser lens (an object lens) 6, detection of the scratch 23a and the foreign material 24 using a signal, which is provided from the photoelectric converter 8a, becomes possible without influencing scattered light detection from the scratch 23a and the foreign material 24.

Moreover, as regards the incident illumination 12a, 12b shown in FIG. 6, not only for the purpose of solving the problem of stray light, but also because it is easy to receive a component having high intensity distribution of scattered light from the scratch 23a in particular, it is possible to acquire high detection sensitivity in comparison with the case where only the oblique illumination 11 is used. This is because intensity of a low order diffraction light component is comparatively high from among a plurality of intensity of scattered light from the scratch 23a. To be more specific, when irradiating from a direction in proximity to a normal line of the wafer surface, the low order diffraction light component is reflected from the wafer 10, which enables easy condensing by the condenser lens 6. However, it is necessary to prevent regular reflection light (diffraction light), which comes from groundwork of the insulation layer and a surface of the insulation layer for example, from being shielded completely, or from being thrown completely into a pupil of the condenser lens 6.

As a result, in comparison with the case where only the oblique illumination 11 is used, detection of the scratch 23a with high sensitivity becomes possible. Thus, using only the vertical illumination 12a or only the pseudo vertical illumination 12b permits inspection of the scratch 23a with high sensitivity to be realized.

By the way, even if the reflection mirror 4c1 is placed in NA of the condenser lens 6, if the reflection mirror 4c1 to be formed has substantially an oval shape so that image formation characteristics are not influenced by the lens 6, etc., it becomes possible to condense scattered light of an area (circular zone area if it is viewed two-dimensionally), which is indicated by oblique lines in FIG. 6(a), by the condenser lens 6 for image formation. However, if existence of the reflection mirror 4c1 in NA of the condenser lens 6 exerts a bad influence upon the image formation characteristics, it is necessary to provide a mechanism by which the reflection mirror 4c1 is moved out of the NA at the time of vertical illumination. In the case of semiconductor inspection, it is necessary to remove dust generating from the defect-inspecting apparatus as much as possible. From this point of view, it is not desirable to provide the moving mechanism above the wafer. However, even in such a case, using the pseudo vertical illumination 12b will solve this problem. In the case of the pseudo vertical illumination 12b, the reflection mirror 4c2 exists outside the NA, which will not exert a bad influence upon the image formation characteristic by any means. Therefore, it is not necessary to provide an extra moving mechanism.

Moreover, if the surface inspecting apparatus for scratch, etc. according to the present invention is used as a foreign-material inspecting apparatus using only oblique illumination, vertical illumination becomes unnecessary. Therefore, the following method is also possible: moving the reflection mirror 4c1 shown in FIG. 6(a) outside; utilizing all NAs of the condenser lens 6 to condense scattered light, which is generated from a foreign material, effectively; and receiving the condensed light using the photoelectric converter 8b. However, in order to prevent dust from being generated without moving the reflection mirror 4c1 outside, the pseudo vertical illumination 12b, of which accuracy of detecting a scratch decreases to some extent, is used as vertical illumination of a surface inspecting apparatus. Additionally, if the means shown in FIGS. 6(c) and 6(d) are used as vertical illumination, even when using it as a foreign-material inspecting apparatus, in which only oblique illumination is used, its application becomes possible by stopping vertical illumination. Moreover, in the case where it is used as the foreign-material inspecting apparatus, in which only oblique illumination is used, when trying to detect a foreign material on a memory cell, on which a periodical wiring pattern is formed, it is necessary to light-shield a diffraction pattern based on diffraction light from a periodical wiring pattern. Therefore, the spatial filters 51, 53 are replaced with linear spatial filters.

Figure 7A:
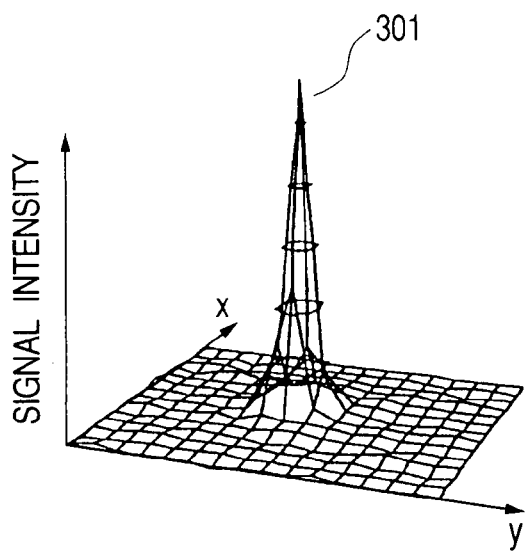
FIGS. 7(a) through 7(c) are diagrams illustrating a luminance signal waveform detected by a detection optical system according to the present invention.
Figure 7B:
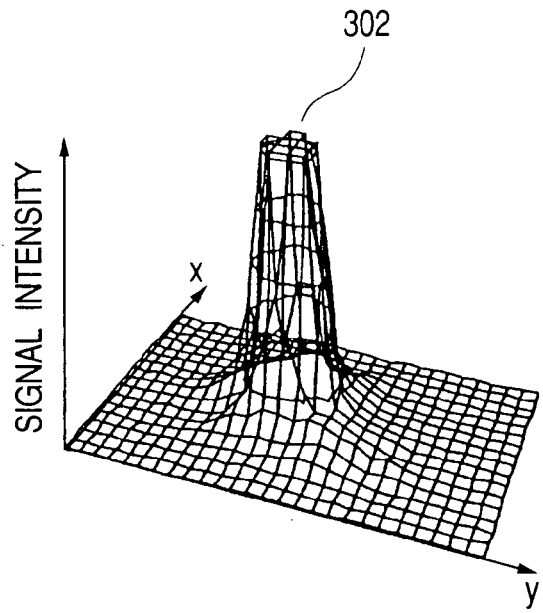
Figure 7C:
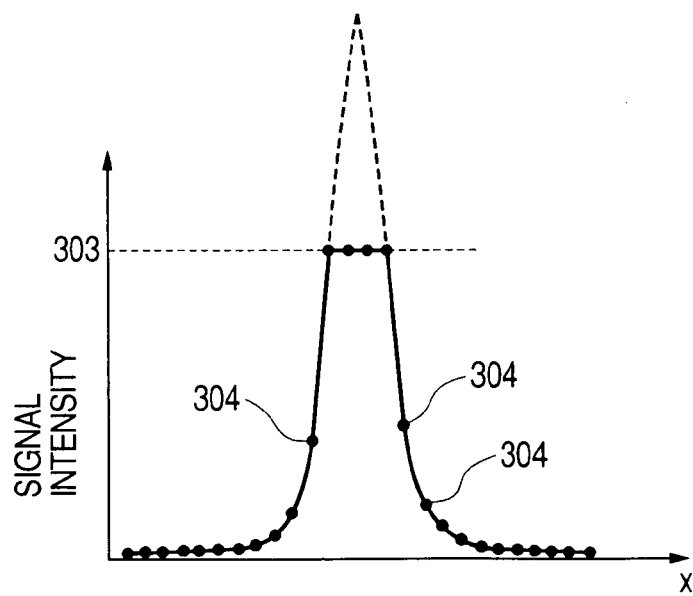

In the next place, a method for estimating a defect size in the comparator 18, etc. according to a luminance signal S(i) for each defect i by the incident illumination 12 and a luminance signal T(i) for each defect i by the oblique illumination 11, which are stored in the storage units 17a, 17b, will be described with reference to FIG. 7. FIGS. 7(a) and 7(b) show waveforms 301, 302 of luminance signals S(i), T(i), which are detected from each of the foreign material 24, the scratch 23a, and the thin film-like foreign material 23b. The luminance signal waveform 302 shown in FIG. 7(b) is saturated at a level of 303, as shown in FIG. 7(c), due to a dynamic range of detectors (photoelectric converters) 8a, 8b. Because of it, the luminance signal waveform 302 is interpolated according to a plot point 304, and the interpolated signal waveform is integrated two-dimensionally to determine its volume. Because the luminance signal shown in FIG. 7(a) is not saturated, the luminance signal waveform is integrated two-dimensionally, as it is, to determine a volume. Because the determined volume values (two-dimensionally integrated values) are in correlation with defect sizes, multiplying this correction coefficient permits estimated data in response to the defect size to be obtained.

Figure 8:
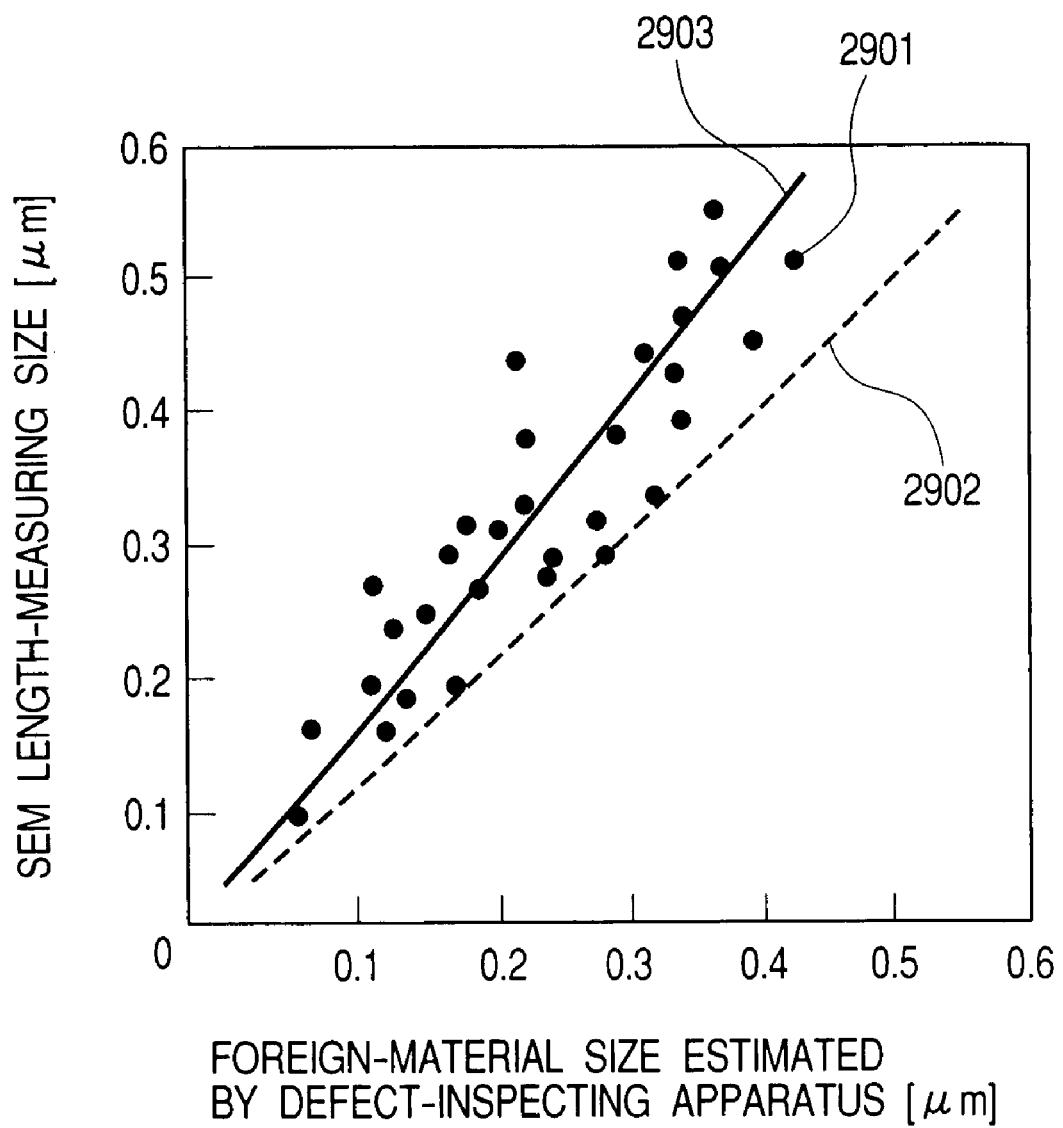
FIG. 8 is a correlation diagram that shows a foreign material made on a CMP surface of a wafer using a correlation between a foreign material size estimated by a defect-inspecting apparatus (μm) and a SEM measured size measured by SEM (μm), according to the present invention.

FIG. 8 shows a relation between a foreign material size (μm), which is estimated as estimated data of a foreign material 2901 by the comparator 18 of the inspection device according to the present invention, and a size (μm) that is actually measured by SEM. As shown in this FIG. 8, because of a plurality of process processing (CMP, for example) processes for the wafer 10, there are different correlations as shown by 2902, 2903. For this reason, the correction coefficient described above will change in response to a surface state of the wafer. Therefore, according to SEM measurement, it is necessary to determine a correction coefficient in response to a product process (a surface state of the wafer) beforehand.

Figure 9A:
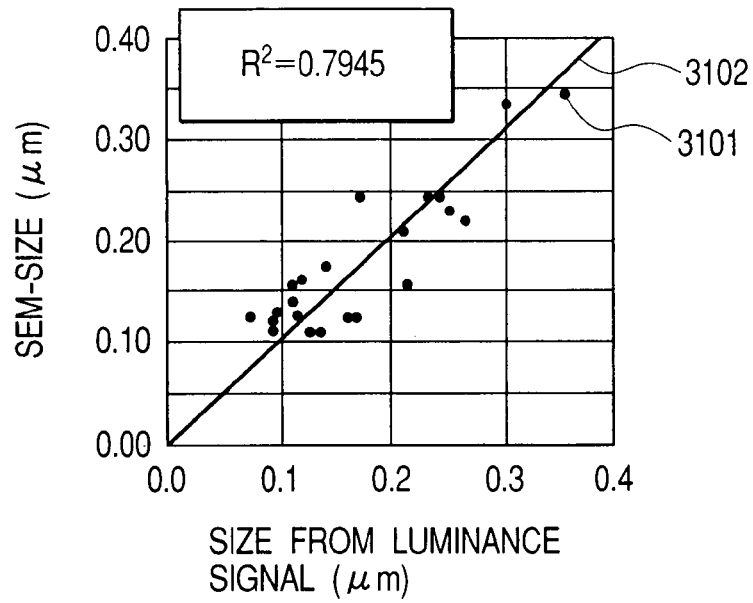
FIGS. 9(a) and 9(b) are correlation diagrams that plots a state in which foreign materials occur, where a horizontal axis indicates a size from a luminance signal (μm) and a vertical axis indicates a SEM measured size (μm) in a front-end process wafer (initial process wafer) and a back-end process wafer (latter-period process wafer), according to the present invention.

In addition, FIG. 9(a) shows that as regards a defect 3101 in a front-end process wafer (a wafer in a transistor formation process, which is an initial process), there is a correlation between a foreign material size estimated from a luminance signal waveform. (μm) and a SEM measured size. (μm) with a correlation coefficient of $R^2=0.7945$ at 3102. In this manner, because extremely small defects ranging from 0.1 to 0.4 μm exert an influence upon performance of a transistor in the transistor formation process, it is found out that even such extremely small defects show a correlation. By the way, the correlation coefficient R is expressed by an expression (Expression 1) as shown below.

$$R=(N\Sigma x_I y_I-(\Sigma x_I)(\Sigma y_I))/(\sqrt{(N\Sigma x_I^2-(\Sigma x_2)(N\Sigma y_I^2-(\Sigma y_I)^2))}) \quad \text{(Expression 1)}$$

where x, y express variates.

Figure 9B:
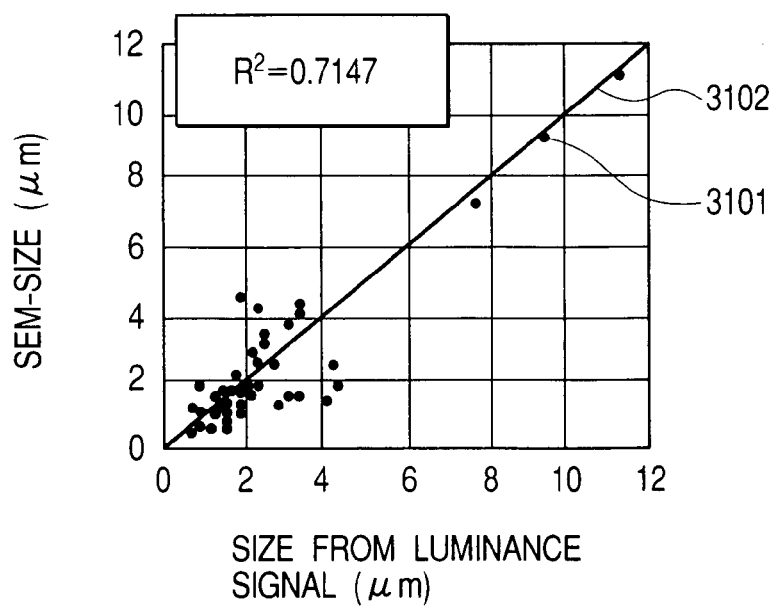

In addition, FIG. 9(b) shows that as regards a defect 3101 in a back-end process wafer (a wafer in a wiring formation process, which is a latter-period process), there is a correlation between a foreign material size estimated from a luminance signal waveform (μm) and a SEM measured size (μm) with a correlation coefficient of $R^2=0.7147$ at 3102. In this manner, because minute foreign materials ranging from 0.3 to about 5 μm or more exert an influence upon wiring in the wiring formation process, it is found out that even such minute defects show a correlation. It is to be noted that because a minute foreign material having a size of 0.3 μm or less has less importance in the wiring process, it is erased.

Figure 10:
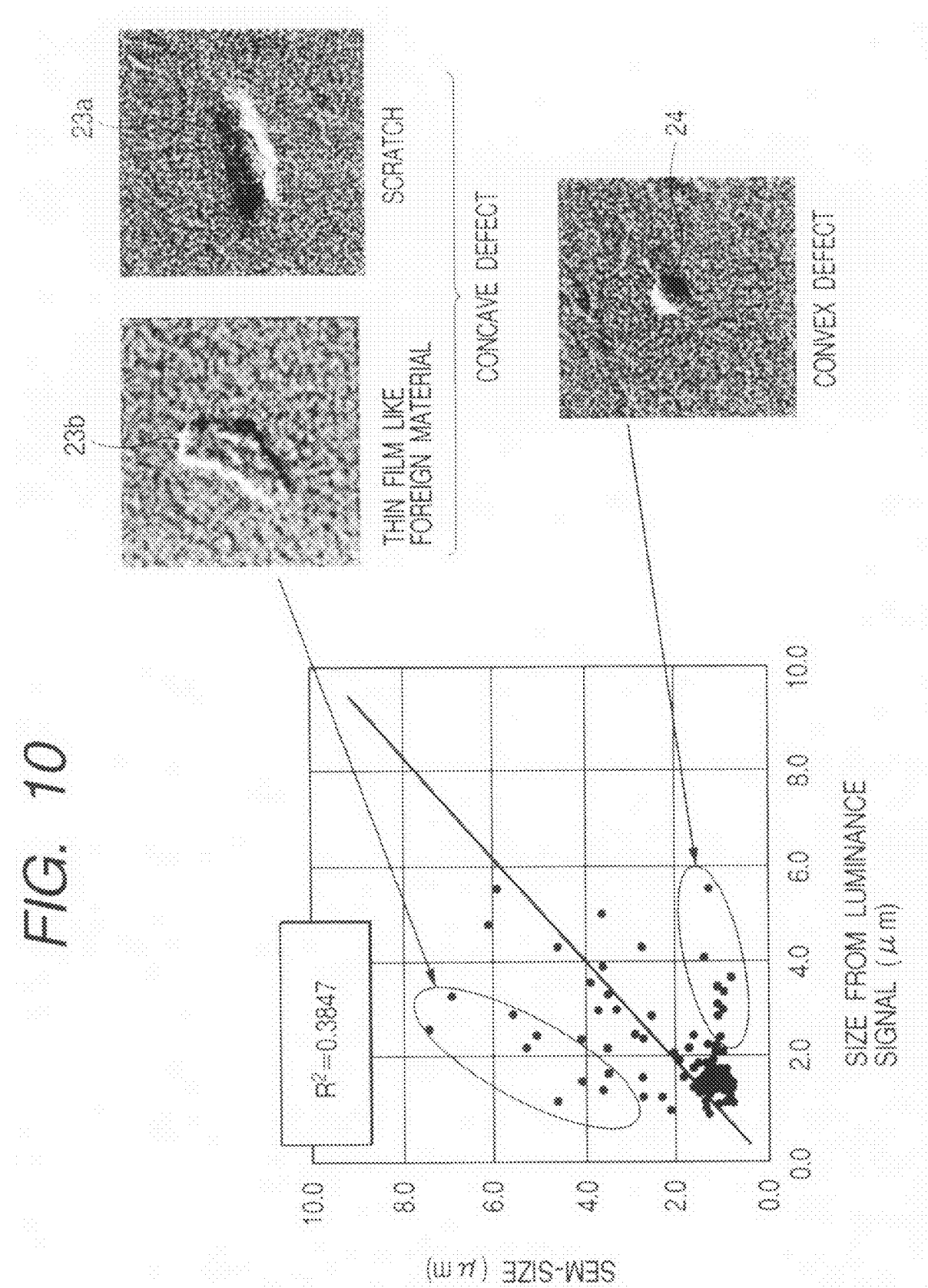
FIG. 10 is a correlation diagram that shows a convex defect (particulate foreign material) and a concave defect (scratch, thin film-like foreign material), which are made on CMP of a wafer, using a correlation between a size (μm) from a luminance signal detected by a defect-inspecting apparatus and a SEM measured size (μm) measured by SEM, according to the present invention.

Next, a defect to be inspected by the inspecting apparatus according to the present invention will be described with reference to FIG. 10. As a defect of a surface on which CMP has been processed, the following exist: the convex defect 24 based on a usual foreign material (approximately ranging from 0.1 to 5 μm); the concave defect 23a based on a scratch (having a width W approximately ranging from 0.2 to 0.4 μm, and a depth D approximately ranging from several nm to several tens nm); and the flat defect 23b, to which a thin film-like foreign material (having a diameter approximately ranging from 0.5 to 2 μm, and a thickness approximately ranging from several nm to several tens nm) adheres.

Moreover, it has been found out that the convex defect 24 was in different correlation with the concave defect 23a and the flat defect 23b judging from a correlation diagram (correlation coefficient $R^2=0.3847$) based on a size from a luminance signal (μm) and a SEM measured size (μm).

In addition, it has been found out that it was possible to discriminate between the concave defect 23a such as scratches and the flat defect 23b such as thin film-like foreign materials according to a defect size, which is estimated from luminance signals S(i), T(i) detected by incident illumination and/or oblique illumination. Furthermore, by checking an area, on which the convex defect 24 such as foreign materials and the concave defect 23a such as scratches are made, to tell whether or not the area is inside a circuit pattern area, or whether or not the area is outside the circuit pattern area, it becomes possible to discriminate fatality of the convex defect 24 such as foreign materials and the concave defect 23a such as scratches to a circuit pattern.

Figure 11:
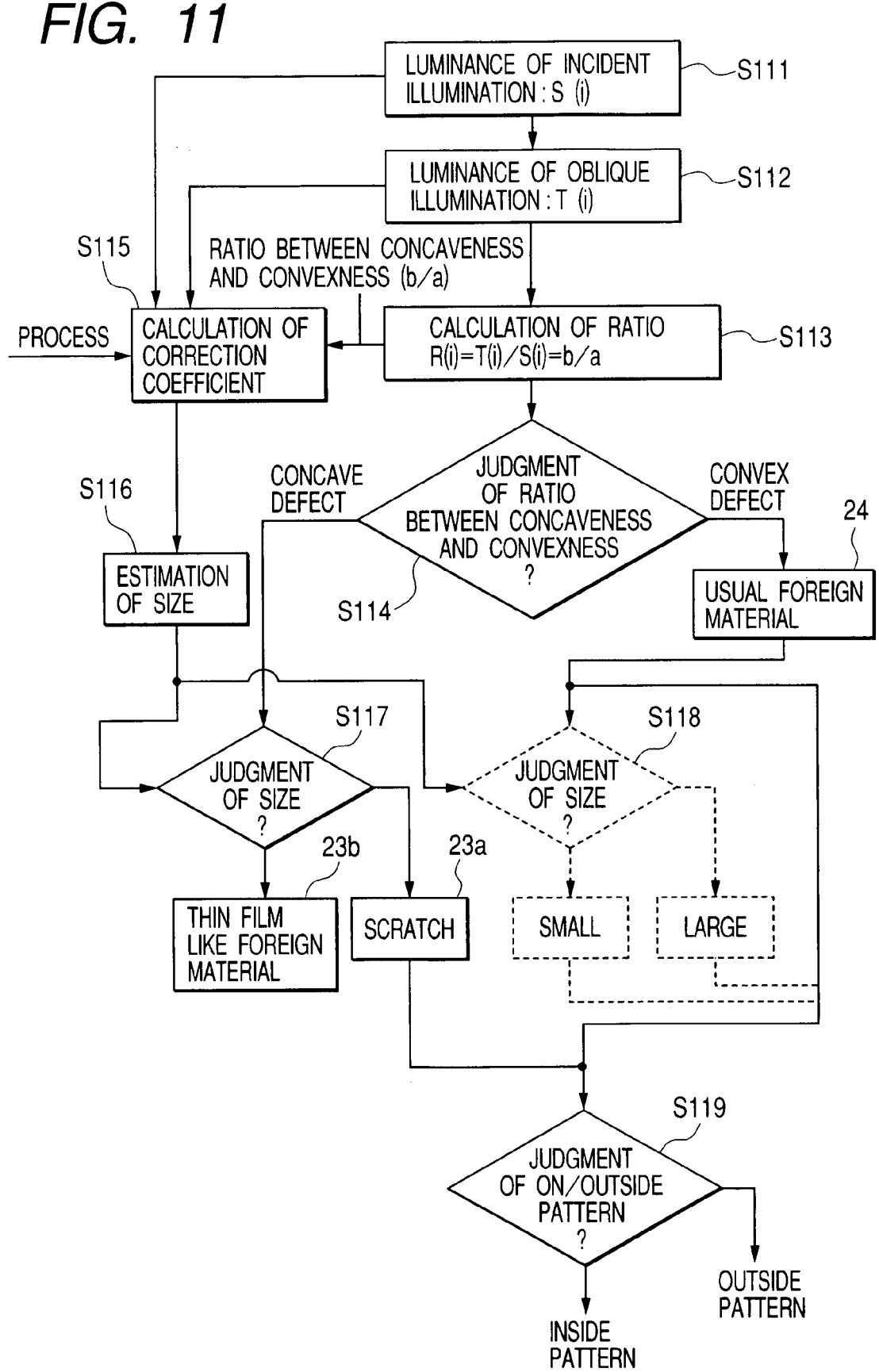
FIG. 11 is a diagram illustrating one example of a process flow of discrimination among a scratch, a thin film-like foreign material, and a particulate foreign material (usual foreign material), according to the present invention.

Therefore, these discrimination methods, by which arithmetic processing is performed using the comparator 18, will be described with reference to FIG. 11. In the first place, in a step S111, a luminance signal S(i) for each defect i by the incident illumination 12, which is detected by the photoelectric converter 8a, is A/D converted using the A/D converter 16a before storing the luminance signal S (i) in the storage unit 17a. At the same time, or after that, in a step S112, a luminance signal T(i) for each defect i by the oblique illumination 11, which is detected by the photoelectric converter 8b, is A/D converted using the A/D converter 16b before storing the luminance signal T (i) in the storage unit 17b. Then, in a step S113, judging from a ratio R(i) of the luminance signal S(i) for each defect i detected by the incident illumination to the luminance signal T(i) for each defect i detected by the oblique illumination, which have been stored in each of the storage units 17a, 17b, the comparator 18 determines a concavo-convex level (b/a) shown in FIG. 12 using an expression (Expression 2) as shown below.

Figure 12:
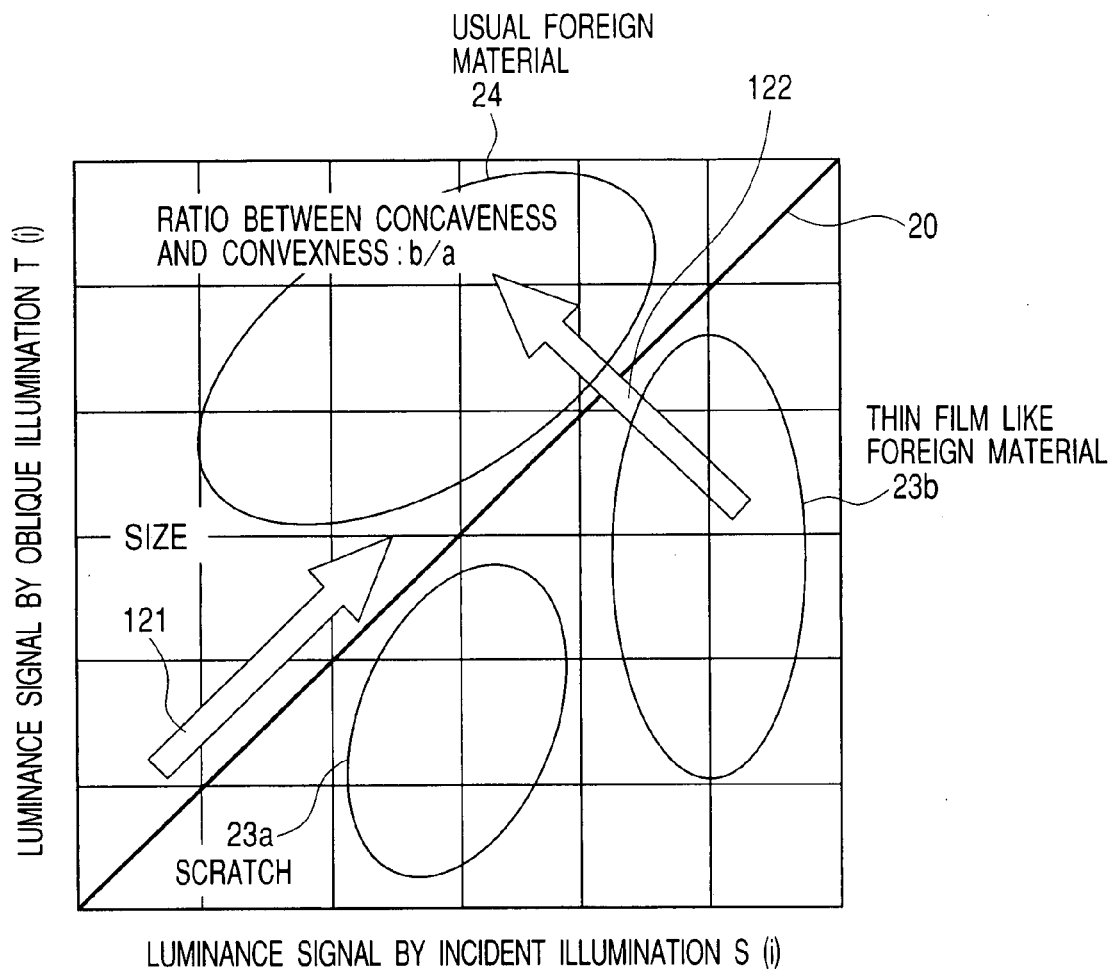
FIG. 12 is a correlation diagram showing basic ideas according to the present invention, explaining that a scratch, a thin film-like foreign material, and a particulate foreign material (usual foreign material) are discriminated according to a concavo-convex level (b/a) and a size based on a relationship between a luminance signal S (i) by incident illumination and a luminance signal T(i) by oblique illumination.
Figure 13:
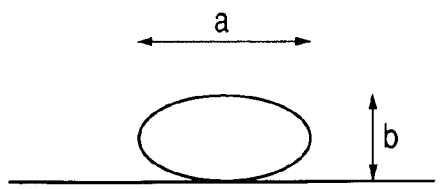
FIG. 13 is an explanatory diagram of a concavo-convex level.

By the way, FIG. 12 is a table of logarithms in which both a horizontal axis and a vertical axis are indicated by logarithms. In this FIG. 12, a direction of an arrow 121, which goes from bottom left to top right, corresponds to a defect size; and an arrow 122, which has a direction at the right angle to the arrow 121, is indicated by a concavo-convex level (b/a) of a defect. The concavo-convex level (b/a) of a defect is indicated by a ratio of a size b of a vertical direction to a size a of a lateral direction shown in FIG. 13. However, the following is not always required: discrimination of the concavo-convex level of the defect, which is based on a ratio of luminance signals (T(i)/S(i)), and discrimination of the defect size, which is based on a multiplied value of an integrated value of the luminance signals (S(i), T(i)) by a correction coefficient in response to a concavo-convex level and a process, take logarithms of the luminance signals respectively.

$$R(i)=T(i)/S(i)=b/a \quad \text{(Expression 2)}$$

In this case, i is a serial number, which is provided for each defect, in order to evaluate several defects. It is to be noted that because there is a case where one defect is detected as a plurality of defects depending on a size of luminous flux d and a pixel size of the photoelectric converter 7, it is necessary to convert a signal, which indicates defects detected at positions close to one another, into a signal, which indicates one defect, using extension processing (connection processing). Because of it, the serial number i, which is provided for each defect, is given to a signal indicating one defect for which connection processing is performed.

Moreover, in a step S114, the comparator 18 performs the following: if the luminance ratio R(i), which has been predetermined as described above, is higher than a predetermined threshold value (a reference value for judgment: the discrimination line 20 shown in FIG. 5), judging the defect to be the convex defect 24 such as a particulate foreign material; and if the luminance ratio R (i) is lower than the predetermined threshold value, judging the defect to be the concave defect 23 such as a scratch and a thin film-like foreign material. In this example, the detected luminance T(i) at the time of the oblique illumination is divided by the detected luminance value S(i) at the time of the incident illumination. However, in contrast with this, the detected luminance value S(i) at the time of the incident illumination may be divided by the detected luminance value T(i) at the time of the oblique illumination. In this case, the defect is judged in the following manner: if the ratio R(i) is higher than the predetermined threshold value (a reference value for judgment: the discrimination line 20 shown in FIG. 5), the defect is judged to be the concave defect 23 such as a scratch and a thin film-like foreign material; and if the ratio R(i) is lower than the predetermined threshold value, the defect can be judged to be the convex defect 24 such as a foreign material.

Next, in a step S115, the total control unit 30 calculates a correction coefficient to estimate data in response to a defect size on the basis of the concavo-convex level (b/a) obtained in the step S113 and process information of the wafer 10 obtained from the process-control computer 101.

Next, in a step S116, the comparator 18 or the total control unit 30 performs the following: on the basis of the luminance signal S(i) for each defect i detected by incident illumination and the luminance signal T(i) for each defect i detected by oblique illumination, which have been stored in each of the storage units 17a, 17b, integrating each luminance signal waveform two-dimensionally to determine a volume value; multiplying the value by the correction coefficient calculated in the total control unit 30, which conforms to a surface state of the wafer (that can be acquired as process information from the process-control computer 101) and the concavo-convex level (b/a); and calculating an estimated value of a defect size (estimated data in response to the size) (μm).

Next, in a step S117, as shown in FIG. 12, the comparator 18 or the total control unit 30 can discriminate the concave defect 23 from the scratch 23a and the thin film-like foreign material 23b on the basis of data in response to the defect size estimated in the step S115. It is to be noted that, as shown in FIG. 12, it is also possible to discriminate between the scratch 23a and the thin film-like foreign material 23b by integrating a waveform of the luminance signal S(i) by incident illumination two-dimensionally to determine a volume value, and by using a multiplied value of the determined volume value by the correction coefficient (estimated data in response to size). using the method described above, discrimination between the scratch 23a, which is a concave defect, and the thin film-like foreign material 23b becomes possible.

Figures 14, 15:
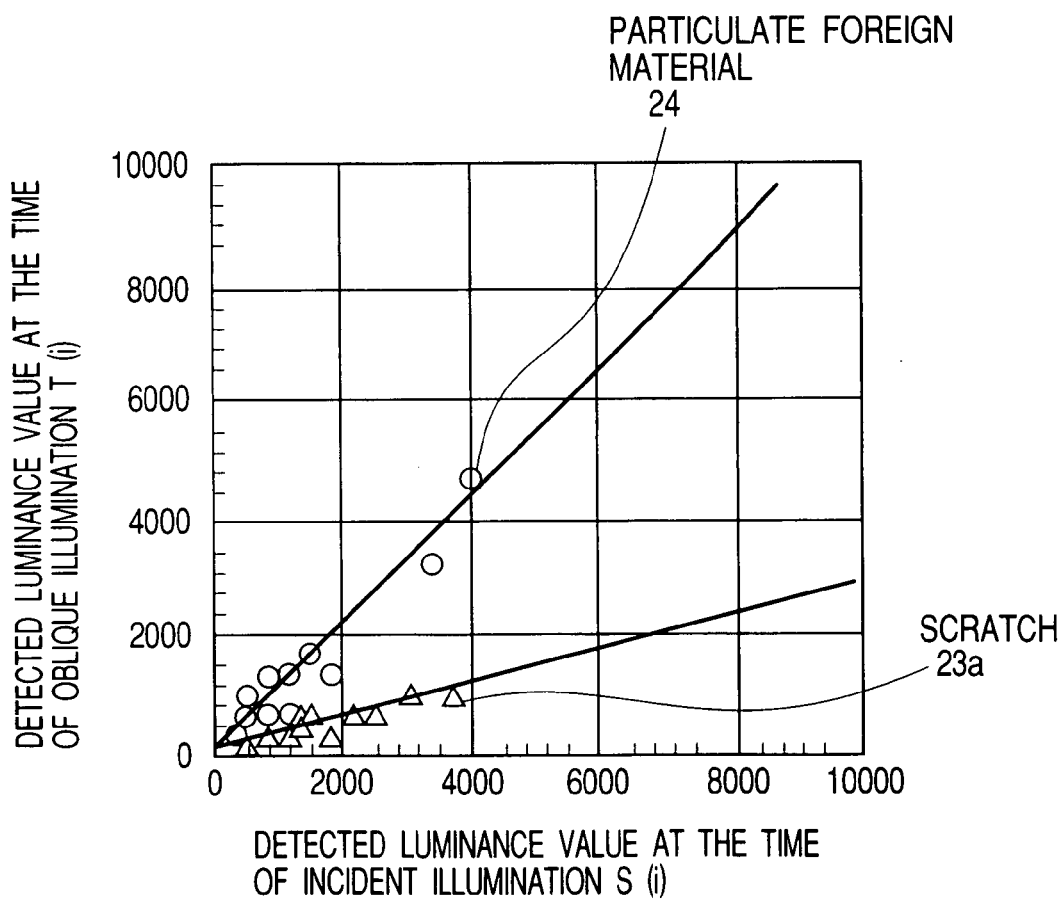
FIG. 14 is an explanatory diagram for obtaining inspection results, which are classified into categories 1 through 5 so that fatality of a defect can be judged, according to the present invention.
FIG. 15 is a diagram illustrating distribution of a particulate foreign material and a scratch on the basis of a relationship between a luminance signal S(i) by incident illumination and a luminance signal T(i) by oblique illumination, according to the present invention.

Next, in the total control unit 30, it is possible to discriminate the usual particulate foreign material 24 as a convex defect discriminated in the step S114. In addition, if it is necessary to classify the discriminated particulate foreign materials according to a size, using a size estimated value of a foreign material (estimated data in response to size), which is obtained from the step S116, in a step S118 permits the discriminated particulate foreign materials to be classified for the purpose of showing them in FIG. 12. Moreover, in a step S119, the comparator 18 or the total control unit 30 can judge fatality of the foreign material 24 and the scratch 23a in relation to a circuit pattern by judging that the particulate foreign material 24 and the scratch 23a are made on the circuit pattern, or that they are made outside the circuit pattern; in this case, as shown in FIG. 14, as regards the small-sized particulate foreign material 24 and the small-sized scratch 23a, the judgment is performed on the basis of configuration information of circuit patterns on the wafer 10, which is obtained through the network 103 from a CAD system (not shown), or on the basis of configuration information of circuit patterns, which is obtained based on an image signal of a circuit pattern detected by the detector 8a, 8b. To be more specific, if the foreign material 24, of which a defect size is small, is made on the circuit pattern, it can be classified as category 1; if the particulate foreign material 24 is made outside the circuit pattern, it can be classified as category 2; if the scratch 23a, of which a defect size is small, is made on the circuit pattern, it can be classified as category 3; if the scratch 23a is made outside the circuit pattern, it can be classified as category 4; and if for example a thin film-like foreign material, of which a defect size is large, is made, it can be classified as category 5. In this manner, the total control unit 30 can classify the defects into the categories by process, at least by lot. Therefore, it is possible to evaluate the fatality of the defect. Additionally, it is also possible to utilize the classification to investigate a cause of the defect. By the way, if configuration information of a circuit pattern is obtained on the basis of an image signal of the circuit pattern, which is detected by the detectors 8a, 8b, the luminance signal S(i), T(i) in relation to the defect can be extracted by performing, for example, repeated chip-comparison or die-comparison of the image signal detected by the detector 8a, 8b to erase the image signal of the repeated circuit pattern.

Figure 16:
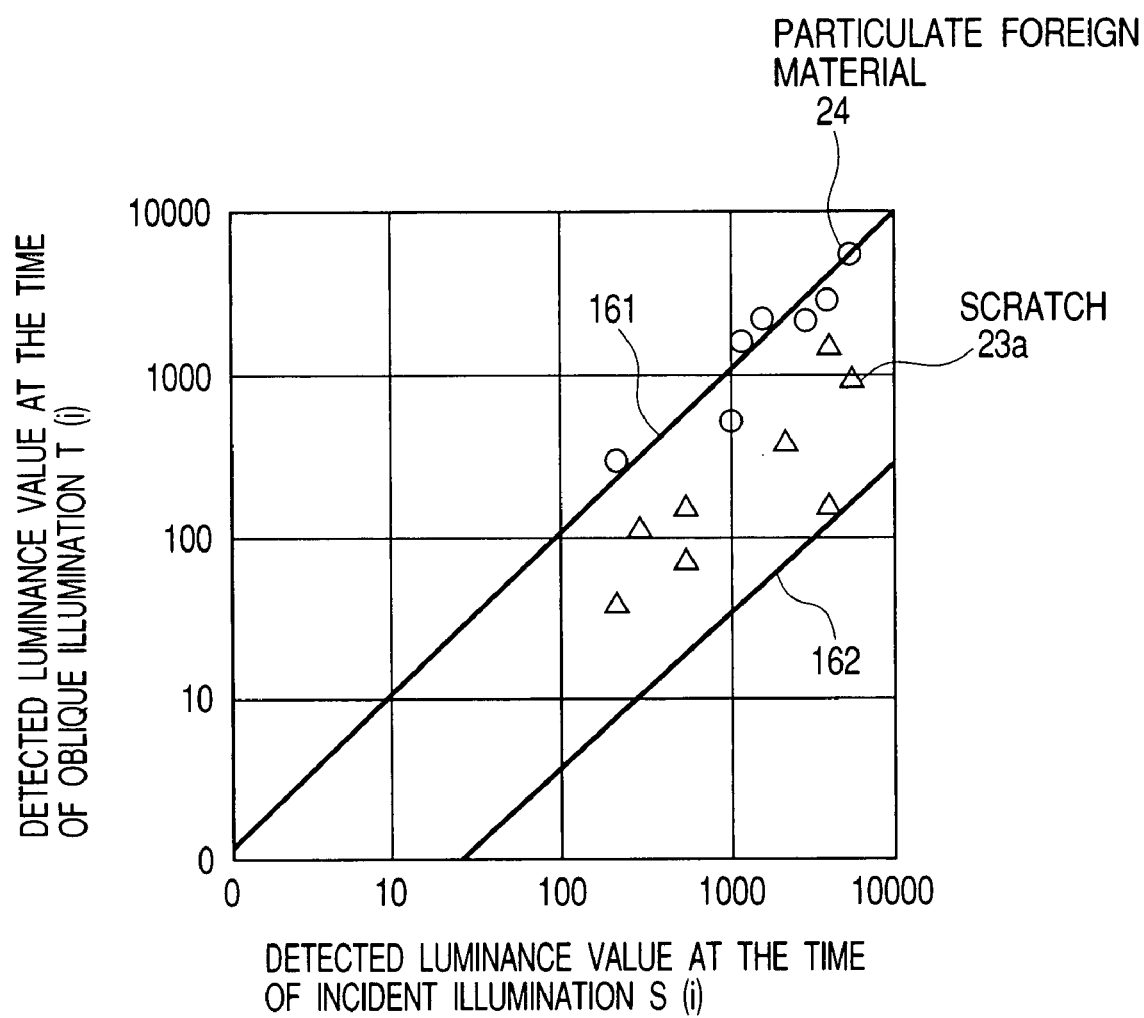
FIG. 16 is a diagram illustrating distribution of a particulate foreign material and a scratch on the basis of a relationship between a logarithm value of a luminance signal S(i) by incident illumination and a logarithm value of a luminance signal T(i) by oblique illumination, according to the present invention.

Next, a correlation diagram illustrating a correlation between the detected luminance value S(i) at the time of the incident illumination and the detected luminance value T(i) at the time of the oblique illumination for a particulate foreign material (shown by ○) or a scratch (shown by △), which are displayed in the display device 33 by the total control unit 30, is shown in FIGS. 15 and 16. As shown in FIG. 16, as compared with a case where the luminance values S(i), T(i) are displayed using a normal scale shown in FIG. 15, taking logarithms for both of the luminance values S(i), T(i) enables easier discrimination between the scratch 23a and the foreign material 24 and easier setting of the threshold value (the discrimination line 20) for discriminating both of the scratch 23a and the foreign material 24 on a screen. It is to be noted that, as shown in FIG. 16, if logarithms are provided for a horizontal axis and a vertical axis, a correlation line 161 indicating the particulate foreign material 24 becomes parallel to a correlation line 162 indicating the scratch 23a.

Figure 17A:
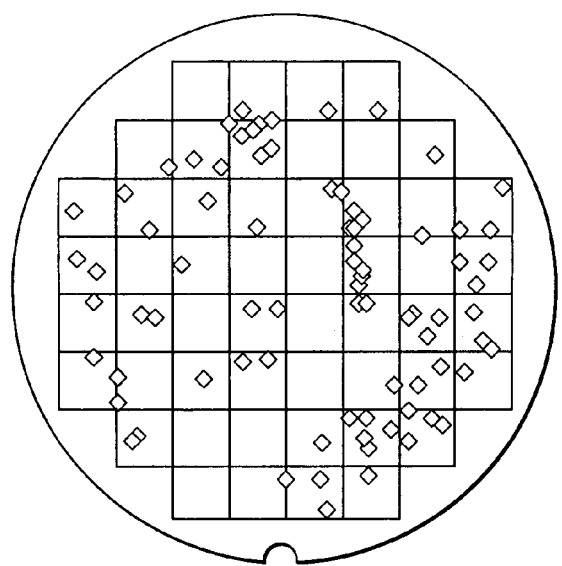
FIGS. 17(a) through 17(c) are diagrams illustrating a wafer map that shows distribution of each defect discriminated by a defect-inspecting apparatus, according to the present invention.
Figure 17B:
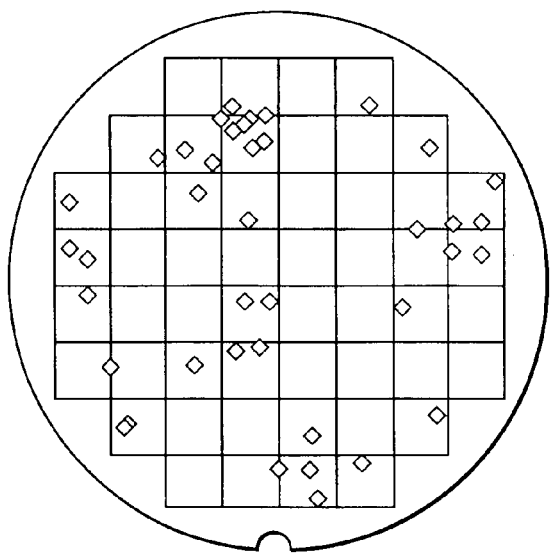
Figure 17C:
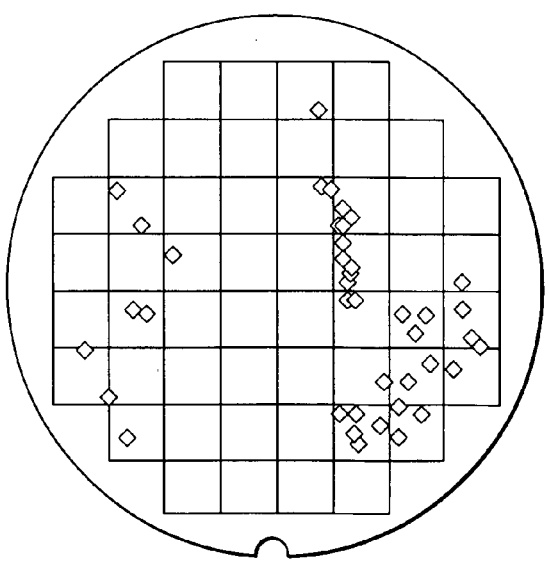

Next, a defect map, which is displayed on a screen of the display device 33 by the total control unit 30, will be described with reference to FIG. 17. FIG. 17(a) shows a state in which a foreign material map of foreign materials on a wafer in a given CMP process is displayed on the screen of the display device 33; this map is a result of an inspection by which the foreign materials are discriminated in the step S114 shown in FIG. 11. In a similar manner, FIG. 17(b) shows a state in which a scratch map of scratches on a wafer in a given CMP process is displayed on the screen of the display device 33; this map is a result of an inspection by which the scratches are discriminated in the step S117 shown in FIG. 11. In a similar manner, FIG. 17(c) shows a state in which a thin film-like foreign material map of thin film-like foreign materials on a wafer in a given CMP process is displayed on the screen of the display device 33; this map is a result of an inspection by which the thin film-like foreign materials are discriminated in the step S117 shown in FIG. 11. Judging from each of the foreign material map, the scratch map, and the thin film-like foreign material map, it is possible to know each generation distribution of the particulate foreign materials, the scratches, and the thin film-like foreign materials on the wafer.

For this reason, supplying each generation distribution information of the particulate foreign materials, the scratches, and the thin film-like foreign materials as feedback to a fabrication process, which performs a polishing process, a grinding process, a washing process, or a sputtering process for an object surface to be processed of a semiconductor device, in order to take appropriate measures enables dramatic improvement of a yield rate in the semiconductor device.

As described above, according to the present invention, the following effect is produced: in semiconductor production and magnetic head production, when the polishing or the grinding process, such as CMP, is performed for an object to be fabricated such as an insulating layer, it is possible to inspect a scratch, etc. showing shape variations, which is produced on the surface, and an adhered particulate foreign material, while discriminating among them.

In addition, according to the present invention, because shapes of scratches are classified in detail, an effect of enabling quick identification of a cause of malfunction is produced.

Moreover, according to the present invention, the following effects are produced: because hundred percent sampling inspection or sampling inspection with high frequency is possible in the planarization polishing process, it is possible to detect malfunction of the polishing device immediately; as a result, appropriate measures can be taken, which enables dramatic improvement of a yield rate in a polishing process.

What is claimed is:

1. A defect-inspecting apparatus comprising:
   a stage on which an object to be inspected is mounted;
   an illumination optical system including:
     a high-angle illumination system which illuminates light on a surface of the object to be inspected with desired luminous flux from a high-angle relative to the surface of the object; and
     a low-angle illumination system which illuminates light on the surface of the object to be inspected with desired luminous flux from a low-angle relative to said high-angle illumination system;
   a detection optical system including:
     a condensing optical system which condenses light scattered from the surface of the object by the illumination of the high-angle illumination system and/or the low-angle illumination system; and
     a light receiving optical unit which detects the scattered light condensed by said condensing optical system and converts the detected light into a first signal corresponding to said light illuminated by said high-angle illumination optical system and/or a second signal corresponding to said light illuminated by said low-angle illumination optical system; and
   a classification unit which utilizes the first and second signal and classifies defects on the object to be inspected, wherein a defect size is estimated by changing a correction coefficient of the defect size on a basis of a concave-convex level (b/a), where the concavo-convex level (b/a) of a defect is indicated by a ratio of a size b of a first direction of the defect to a size a of a second direction of the defect, where the second direction is lateral to the first direction.

2. A defect-inspecting apparatus according to claim 1, where the second direction is substantially orthogonal to the first direction.

3. A defect-inspecting apparatus according to claim 1, wherein:
   the high-angle illumination system of the illumination optical system is configured so that stray light is not generated from the image information optical system.

4. A defect-inspecting apparatus according to claim 1, wherein:
   the detection optical system comprises a shielding optical element which shields a specific light image, which is caused by first reflection light generated from a point high-angle incident-illuminated by the high-angle illumination system, on a Fourier transformed surface of the first reflection light emitted from the point.

5. A defect-inspecting apparatus according to claim 1, wherein:
   the classification unit is configured to classify concave defects into scratches and thin film-like foreign materials on a basis of data in response to a defect size calculated from the first signal and the second signal.

* * * * *

UNITED STATES PATENT AND TRADEMARK OFFICE
CERTIFICATE OF CORRECTION

| | |
|---|---|
| PATENT NO. | : 7,315,366 B2 |
| APPLICATION NO. | : 11/714196 |
| DATED | : January 1, 2008 |
| INVENTOR(S) | : Hamamatsu et al. |

It is certified that error appears in the above-identified patent and that said Letters Patent is hereby corrected as shown below:

Title Page, Item (73) Assignee: should read,

--(73) Assignees: Hitachi, Ltd., Tokyo (JP) and Hitachi High-Technologies Corporation, Tokyo (JP)--.

Signed and Sealed this

Thirteenth Day of July, 2010

David J. Kappos
*Director of the United States Patent and Trademark Office*